(12) United States Patent
Andersen et al.

(10) Patent No.: US 7,867,746 B2
(45) Date of Patent: Jan. 11, 2011

(54) ALPHA-AMYLASE VARIANTS

(75) Inventors: Carsten Andersen, Vaerlose (DK); Christel Thea Jorgensen, Kobenhavn O (DK); Henrik Bisgard-Frantzen, Bagsvaerd (DK); Allan Svendsen, Birkerod (DK); Soren Kjaerulff, Vanlose (DK)

(73) Assignee: Novozymes A/S, Bagsvaerd (DK)

( * ) Notice: Subject to any disclaimer, the term of this patent is extended or adjusted under 35 U.S.C. 154(b) by 151 days.

(21) Appl. No.: 11/934,136

(22) Filed: Nov. 2, 2007

(65) Prior Publication Data

US 2009/0155882 A1    Jun. 18, 2009

Related U.S. Application Data

(62) Division of application No. 10/146,327, filed on May 15, 2002, now Pat. No. 7,306,936, which is a division of application No. 09/537,168, filed on Mar. 29, 2000, now Pat. No. 6,410,295.

(60) Provisional application No. 60/127,427, filed on Apr. 1, 1999.

(30) Foreign Application Priority Data

Mar. 30, 1999 (DK) .............................. 1999 00437

(51) Int. Cl.
*C12N 9/00* (2006.01)
*C12N 9/28* (2006.01)
*C12N 1/20* (2006.01)
*C12N 15/00* (2006.01)
*C07H 21/04* (2006.01)

(52) U.S. Cl. .................... 435/202; 435/183; 435/252.3; 435/320.1; 536/23.2

(58) Field of Classification Search ....................... None
See application file for complete search history.

(56) References Cited

U.S. PATENT DOCUMENTS

| 5,753,460 | A | 5/1998 | Bisgard-Frantzen |
| 5,989,169 | A | 11/1999 | Svendsen et al. |
| 6,022,724 | A | 2/2000 | Svendsen et al. |
| 6,093,562 | A | 7/2000 | Frantzen et al. |
| 6,204,232 | B1 | 3/2001 | Borchert et al. |
| 6,297,038 | B1 | 10/2001 | Frantzen et al. |
| 6,440,716 | B1 | 8/2002 | Svendsen et al. |
| 6,673,589 | B2 | 1/2004 | Borchert et al. |
| 6,867,031 | B2 | 3/2005 | Bisgaard-Frantzen et al. |
| 2001/0039253 | A1 | 11/2001 | Borchert et al. |
| 2003/0170769 | A1 | 9/2003 | Svendsen et al. |
| 2004/0038368 | A1 | 2/2004 | Borchert et al. |
| 2004/0048351 | A1 | 3/2004 | Svendsen et al. |

FOREIGN PATENT DOCUMENTS

| EP | 285123 | 5/1988 |
| WO | WO 90/11352 | 10/1990 |
| WO | WO 91/00353 | 1/1991 |
| WO | WO 94/18314 | 8/1994 |
| WO | WO 95/10603 | 4/1995 |
| WO | WO 95/26397 | 10/1995 |
| WO | WO 96/23873 | 8/1996 |
| WO | WO 96/23874 | 8/1996 |
| WO | WO 97/41213 | 11/1997 |
| WO | WO 98/26078 | 6/1998 |
| WO | WO 99/09183 | 2/1999 |
| WO | WO 01/88107 | 11/2001 |
| WO | WO 02/092797 | 11/2002 |

OTHER PUBLICATIONS

Accession AAR72449. Dec. 1, 1995.*
Chica et al. Curr Opin Biotechnol. Aug. 2005;16(4):378-84.*
Sen et al. Appl Biochem Biotechnol. Dec. 2007;143(3):212-23.*
Tsukamoto et al., "Nucleotide Sequence of the Malthohexaose-Producing Amylase Gene From an Alkalophilc *Bacillus* Sp. 707 and Structural Similarity to Liquiefying Type Alpha-Amylases", Biochemical and Biophysical research Communications, Academic Press Inc. , vol. 151, No. 1, pp. 25-31 (1988).
Svensson, "Protein Engineering in the Alpha-Amylase Family: Catalytic Mechanism, Substrate Specificity, and Stability", Plant Molecular Biology, vol. 25, pp. 141-157 (1994).
Holm et al., "Random Mutagenesis Used to Probe the Structure and Function of *Bacillus stearothermophilus* Alpha-Amylase", Protein Engineering, vol. 3, No. 3, pp. 181-191 (1990).
Machius et al., "Crystal Structure of Calcium-Depleted *Bacillus licheniformis* Alpha-Amylase at 2.2 A Resolution". Journal of Molecular Biology, vol. 246, pp. 545-559 (1995).

* cited by examiner

*Primary Examiner*—Christian L Fronda
(74) *Attorney, Agent, or Firm*—Elias Lambiris

(57) ABSTRACT

The invention relates to a variant of a parent Termamyl-like alpha-amylase, which variant exhibits altered properties, in particular reduced capability of cleaving a substrate close to the branching point, and improved substrate specificity and/or improved specific activity relative to the parent alpha-amylase.

22 Claims, No Drawings

SEQUENCE LISTING

<160> NUMBER OF SEQ ID NOS: 40

<210> SEQ ID NO 1
<211> LENGTH: 1443
<212> TYPE: DNA
<213> ORGANISM: Bacillus amyloliquefaciens
<220> FEATURE:
<221> NAME/KEY: CDS
<222> LOCATION: (1)...(1443)

<400> SEQUENCE: 1

```
gta aat ggc acg ctg atg cag tat ttt gaa tgg tat acg ccg aac gac      48
Val Asn Gly Thr Leu Met Gln Tyr Phe Glu Trp Tyr Thr Pro Asn Asp
 1               5                  10                  15 ggc cag cat tgg aaa cga ttg cag aat gat gcg gaa cat tta tcg gat      96
Gly Gln His Trp Lys Arg Leu Gln Asn Asp Ala Glu His Leu Ser Asp
             20                  25                  30 atc ggt att act gcc gtc tgg att ccc ccg gca tat aag gga acg agc     144
Ile Gly Ile Thr Ala Val Trp Ile Pro Pro Ala Tyr Lys Gly Thr Ser
         35                  40                  45 caa gcg gat gtg ggc tac ggt gct tac gac ctt tat gat tta ggg gag     192
Gln Ala Asp Val Gly Tyr Gly Ala Tyr Asp Leu Tyr Asp Leu Gly Glu
     50                  55                  60 ttt cat caa aaa ggg acg gtt cgg aca aag tac gga aca aaa gga gag     240
Phe His Gln Lys Gly Thr Val Arg Thr Lys Tyr Gly Thr Lys Gly Glu
 65                  70                  75                  80 ctg caa tct gcg atc aaa agt ctt cat tcc cgc gac att aac gtt tac     288
Leu Gln Ser Ala Ile Lys Ser Leu His Ser Arg Asp Ile Asn Val Tyr
                 85                  90                  95 ggg gat gtg gtc atc aac cac aaa ggc ggc gct gat gcg acc gaa gat     336
Gly Asp Val Val Ile Asn His Lys Gly Gly Ala Asp Ala Thr Glu Asp
            100                 105                 110 gta acc gcg gtt gaa gtc gat ccc gct gac cgc aac cgc gta att tca     384
Val Thr Ala Val Glu Val Asp Pro Ala Asp Arg Asn Arg Val Ile Ser
        115                 120                 125 gga gaa cac cta att aaa gcc tgg aca cat ttt cat ttt ccg ggg cgc     432
Gly Glu His Leu Ile Lys Ala Trp Thr His Phe His Phe Pro Gly Arg
    130                 135                 140 ggc agc aca tac agc gat ttt aag tgg tat tgg tac cat ttt gac gga     480
Gly Ser Thr Tyr Ser Asp Phe Lys Trp Tyr Trp Tyr His Phe Asp Gly
145                 150                 155                 160 acc gat tgg gac gag tcc cga aag ctg aac cgc atc tat aag ttt caa     528
Thr Asp Trp Asp Glu Ser Arg Lys Leu Asn Arg Ile Tyr Lys Phe Gln
                165                 170                 175 ggg aag act tgg gat tgg gaa gtt tcc aat gaa ttc ggc aac tat gat     576
Gly Lys Thr Trp Asp Trp Glu Val Ser Asn Glu Phe Gly Asn Tyr Asp
            180                 185                 190
```

| | | |
|---|---|---|
| tat ttg atg tat gcc gac ttt gat tat gac cat cct gat gtc gta gca<br>Tyr Leu Met Tyr Ala Asp Phe Asp Tyr Asp His Pro Asp Val Val Ala<br>        195                    200                  205 | 624 | |
| gag att aag aga tgg ggc act tgg tat gcc aat gaa ctg caa ttg gac<br>Glu Ile Lys Arg Trp Gly Thr Trp Tyr Ala Asn Glu Leu Gln Leu Asp<br>210                    215                    220 | 672 | |
| ggt ttc cgt ctt gat gct gtc aaa cac att aaa ttt tct ttt ttg cgg<br>Gly Phe Arg Leu Asp Ala Val Lys His Ile Lys Phe Ser Phe Leu Arg<br>225                    230                235              240 | 720 | |
| gat tgg gtt aat cat gtc agg gaa aaa acg ggg aag gaa atg ttt acg<br>Asp Trp Val Asn His Val Arg Glu Lys Thr Gly Lys Glu Met Phe Thr<br>              245                250                255 | 768 | |
| gta gct gag tac tgg tcg aat gac ttg ggc gcg ctg gaa aac tat ttg<br>Val Ala Glu Tyr Trp Ser Asn Asp Leu Gly Ala Leu Glu Asn Tyr Leu<br>        260                    265                270 | 816 | |
| aac aaa aca aat ttt aat cat tca gtg ttt gac gtg ccg ctt cat tat<br>Asn Lys Thr Asn Phe Asn His Ser Val Phe Asp Val Pro Leu His Tyr<br>        275                    280                285 | 864 | |
| cag ttc cat gct gca tcg aca cag gga ggc ggc tat gat atg agg aaa<br>Gln Phe His Ala Ala Ser Thr Gln Gly Gly Gly Tyr Asp Met Arg Lys<br>290                    295                300 | 912 | |
| ttg ctg aac ggt acg gtc gtt tcc aag cat ccg ttg aaa tcg gtt aca<br>Leu Leu Asn Gly Thr Val Val Ser Lys His Pro Leu Lys Ser Val Thr<br>305                    310                315              320 | 960 | |
| ttt gtc gat aac cat gat aca cag ccg ggg caa tcg ctt gag tcg act<br>Phe Val Asp Asn His Asp Thr Gln Pro Gly Gln Ser Leu Glu Ser Thr<br>              325                330                335 | 1008 | |
| gtc caa aca tgg ttt aag ccg ctt gct tac gct ttt att ctc aca agg<br>Val Gln Thr Trp Phe Lys Pro Leu Ala Tyr Ala Phe Ile Leu Thr Arg<br>        340                    345                350 | 1056 | |
| gaa tct gga tac cct cag gtt ttc tac ggg gat atg tac ggg acg aaa<br>Glu Ser Gly Tyr Pro Gln Val Phe Tyr Gly Asp Met Tyr Gly Thr Lys<br>        355                    360                365 | 1104 | |
| gga gac tcc cag cgc gaa att cct gcc ttg aaa cac aaa att gaa ccg<br>Gly Asp Ser Gln Arg Glu Ile Pro Ala Leu Lys His Lys Ile Glu Pro<br>370                    375                380 | 1152 | |
| atc tta aaa gcg aga aaa cag tat gcg tac gga gca cag cat gat tat<br>Ile Leu Lys Ala Arg Lys Gln Tyr Ala Tyr Gly Ala Gln His Asp Tyr<br>385                    390                395              400 | 1200 | |
| ttc gac cac cat gac att gtc ggc tgg aca agg gaa ggc gac agc tcg<br>Phe Asp His His Asp Ile Val Gly Trp Thr Arg Glu Gly Asp Ser Ser<br>              405                410                415 | 1248 | |
| gtt gca aat tca ggt ttg gcg gca tta ata aca gac gga ccc ggt ggg<br>Val Ala Asn Ser Gly Leu Ala Ala Leu Ile Thr Asp Gly Pro Gly Gly<br>        420                    425                430 | 1296 | |
| gca aag cga atg tat gtc ggc cgg caa aac gcc ggt gag aca tgg cat<br>Ala Lys Arg Met Tyr Val Gly Arg Gln Asn Ala Gly Glu Thr Trp His<br>        435                    440                445 | 1344 | |
| gac att acc gga aac cgt tcg gag ccg gtt gtc atc aat tcg gaa ggc<br>Asp Ile Thr Gly Asn Arg Ser Glu Pro Val Val Ile Asn Ser Glu Gly<br>        450                    455                460 | 1392 | |
| tgg gga gag ttt cac gta aac ggc ggg tcg gtt tca att tat gtt caa<br>Trp Gly Glu Phe His Val Asn Gly Gly Ser Val Ser Ile Tyr Val Gln<br>465                    470                475              480 | 1440 | |
| aga<br>Arg | 1443 | |

<210> SEQ ID NO 2
<211> LENGTH: 481
<212> TYPE: PRT

<213> ORGANISM: Bacillus amyloliquefaciens

<400> SEQUENCE: 2

```
Val Asn Gly Thr Leu Met Gln Tyr Phe Glu Trp Tyr Thr Pro Asn Asp
  1               5                  10                  15

Gly Gln His Trp Lys Arg Leu Gln Asn Asp Ala Glu His Leu Ser Asp
             20                  25                  30

Ile Gly Ile Thr Ala Val Trp Ile Pro Pro Ala Tyr Lys Gly Thr Ser
         35                  40                  45

Gln Ala Asp Val Gly Tyr Gly Ala Tyr Asp Leu Tyr Asp Leu Gly Glu
     50                  55                  60

Phe His Gln Lys Gly Thr Val Arg Thr Lys Tyr Gly Thr Lys Gly Glu
 65                  70                  75                  80

Leu Gln Ser Ala Ile Lys Ser Leu His Ser Arg Asp Ile Asn Val Tyr
                 85                  90                  95

Gly Asp Val Val Ile Asn His Lys Gly Gly Ala Asp Ala Thr Glu Asp
            100                 105                 110

Val Thr Ala Val Glu Val Asp Pro Ala Asp Arg Asn Arg Val Ile Ser
        115                 120                 125

Gly Glu His Leu Ile Lys Ala Trp Thr His Phe His Phe Pro Gly Arg
    130                 135                 140

Gly Ser Thr Tyr Ser Asp Phe Lys Trp Tyr Trp Tyr His Phe Asp Gly
145                 150                 155                 160

Thr Asp Trp Asp Glu Ser Arg Lys Leu Asn Arg Ile Tyr Lys Phe Gln
                165                 170                 175

Gly Lys Thr Trp Asp Trp Glu Val Ser Asn Glu Phe Gly Asn Tyr Asp
            180                 185                 190

Tyr Leu Met Tyr Ala Asp Phe Asp Tyr Asp His Pro Asp Val Val Ala
        195                 200                 205

Glu Ile Lys Arg Trp Gly Thr Trp Tyr Ala Asn Glu Leu Gln Leu Asp
    210                 215                 220

Gly Phe Arg Leu Asp Ala Val Lys His Ile Lys Phe Ser Phe Leu Arg
225                 230                 235                 240

Asp Trp Val Asn His Val Arg Glu Lys Thr Gly Lys Glu Met Phe Thr
                245                 250                 255

Val Ala Glu Tyr Trp Ser Asn Asp Leu Gly Ala Leu Glu Asn Tyr Leu
            260                 265                 270

Asn Lys Thr Asn Phe Asn His Ser Val Phe Asp Val Pro Leu His Tyr
        275                 280                 285

Gln Phe His Ala Ala Ser Thr Gln Gly Gly Gly Tyr Asp Met Arg Lys
    290                 295                 300

Leu Leu Asn Gly Thr Val Val Ser Lys His Pro Leu Lys Ser Val Thr
305                 310                 315                 320

Phe Val Asp Asn His Asp Thr Gln Pro Gly Gln Ser Leu Glu Ser Thr
                325                 330                 335

Val Gln Thr Trp Phe Lys Pro Leu Ala Tyr Ala Phe Ile Leu Thr Arg
            340                 345                 350

Glu Ser Gly Tyr Pro Gln Val Phe Tyr Gly Asp Met Tyr Gly Thr Lys
        355                 360                 365

Gly Asp Ser Gln Arg Glu Ile Pro Ala Leu Lys His Lys Ile Glu Pro
    370                 375                 380

Ile Leu Lys Ala Arg Lys Gln Tyr Ala Tyr Gly Ala Gln His Asp Tyr
385                 390                 395                 400
```

```
                                                        -continued

Phe Asp His His Asp Ile Val Gly Trp Thr Arg Glu Gly Asp Ser Ser
            405                 410                 415

Val Ala Asn Ser Gly Leu Ala Ala Leu Ile Thr Asp Gly Pro Gly Gly
        420                 425                 430

Ala Lys Arg Met Tyr Val Gly Arg Gln Asn Ala Gly Glu Thr Trp His
    435                 440                 445

Asp Ile Thr Gly Asn Arg Ser Glu Pro Val Val Ile Asn Ser Glu Gly
    450                 455                 460

Trp Gly Glu Phe His Val Asn Gly Gly Ser Val Ser Ile Tyr Val Gln
465                 470                 475                 480

Arg

<210> SEQ ID NO 3
<211> LENGTH: 1920
<212> TYPE: DNA
<213> ORGANISM: Bacillus licheniformis
<220> FEATURE:
<221> NAME/KEY: CDS
<222> LOCATION: (421)...(1872)

<400> SEQUENCE: 3
cggaagattg gaagtacaaa aataagcaaa agattgtcaa tcatgtcatg agccatgcgg      60
gagacggaaa atcgtctta atgcacgata tttatgcaac gttcgcagat gctgctgaag     120
agattattaa aaagctgaaa gcaaaaggct atcaattggt aactgtatct cagcttgaag     180
aagtgaagaa gcagagaggc tattgaataa atgagtagaa cgccatatc ggcgcttttc      240 ttttggaaga aaatataggg aaaatggtac ttgttaaaaa ttcggaatat ttatacaaca     300
tcatatgttt cacattgaaa ggggaggaga atcatgaaac aacaaaaacg gctttacgcc     360
cgattgctga cgctgttatt tgcgctcatc ttcttgctgc ctcattctgc agcagcggcg     420 gca aat ctt aat ggg acg ctg atg cag tat ttt gaa tgg tac atg ccc      468
Ala Asn Leu Asn Gly Thr Leu Met Gln Tyr Phe Glu Trp Tyr Met Pro
 1               5                  10                  15 aat gac ggc caa cat tgg agg cgt ttg caa aac gac tcg gca tat ttg      516
Asn Asp Gly Gln His Trp Arg Arg Leu Gln Asn Asp Ser Ala Tyr Leu
                 20                  25                  30 gct gaa cac ggt att act gcc gtc tgg att ccc ccg gca tat aag gga      564
Ala Glu His Gly Ile Thr Ala Val Trp Ile Pro Pro Ala Tyr Lys Gly
             35                  40                  45 acg agc caa gcg gat gtg ggc tac ggt gct tac gac ctt tat gat tta      612
Thr Ser Gln Ala Asp Val Gly Tyr Gly Ala Tyr Asp Leu Tyr Asp Leu
         50                  55                  60 ggg gag ttt cat caa aaa ggg acg gtt cgg aca aag tac ggc aca aaa      660
Gly Glu Phe His Gln Lys Gly Thr Val Arg Thr Lys Tyr Gly Thr Lys
 65                  70                  75                  80 gga gag ctg caa tct gcg atc aaa agt ctt cat tcc cgc gac att aac      708
Gly Glu Leu Gln Ser Ala Ile Lys Ser Leu His Ser Arg Asp Ile Asn
                 85                  90                  95 gtt tac ggg gat gtg gtc atc aac cac aaa ggc ggc gct gat gcg acc      756
Val Tyr Gly Asp Val Val Ile Asn His Lys Gly Gly Ala Asp Ala Thr
                100                 105                 110 gaa gat gta acc gcg gtt gaa gtc gat ccc gct gac cgc aac cgc gta      804
Glu Asp Val Thr Ala Val Glu Val Asp Pro Ala Asp Arg Asn Arg Val
            115                 120                 125 att tca gga gaa cac cta att aaa gcc tgg aca cat ttt cat ttt ccg      852
Ile Ser Gly Glu His Leu Ile Lys Ala Trp Thr His Phe His Phe Pro
        130                 135                 140 ggg cgc ggc agc aca tac agc gat ttt aaa tgg cat tgg tac cat ttt      900
```

```
Gly Arg Gly Ser Thr Tyr Ser Asp Phe Lys Trp His Trp Tyr His Phe
145                 150                 155                 160 gac gga acc gat tgg gac gag tcc cga aag ctg aac cgc atc tat aag    948
Asp Gly Thr Asp Trp Asp Glu Ser Arg Lys Leu Asn Arg Ile Tyr Lys
                165                 170                 175 ttt caa gga aag gct tgg gat tgg gaa gtt tcc aat gaa aac ggc aac    996
Phe Gln Gly Lys Ala Trp Asp Trp Glu Val Ser Asn Glu Asn Gly Asn
            180                 185                 190 tat gat tat ttg atg tat gcc gac atc gat tat gac cat cct gat gtc   1044
Tyr Asp Tyr Leu Met Tyr Ala Asp Ile Asp Tyr Asp His Pro Asp Val
        195                 200                 205 gca gca gaa att aag aga tgg ggc act tgg tat gcc aat gaa ctg caa   1092
Ala Ala Glu Ile Lys Arg Trp Gly Thr Trp Tyr Ala Asn Glu Leu Gln
    210                 215                 220 ttg gac ggt ttc cgt ctt gat gct gtc aaa cac att aaa ttt tct ttt   1140
Leu Asp Gly Phe Arg Leu Asp Ala Val Lys His Ile Lys Phe Ser Phe
225                 230                 235                 240 ttg cgg gat tgg gtt aat cat gtc agg gaa aaa acg ggg aag gaa atg   1188
Leu Arg Asp Trp Val Asn His Val Arg Glu Lys Thr Gly Lys Glu Met
                245                 250                 255 ttt acg gta gct gaa tat tgg cag aat gac ttg ggc gcg ctg gaa aac   1236
Phe Thr Val Ala Glu Tyr Trp Gln Asn Asp Leu Gly Ala Leu Glu Asn
            260                 265                 270 tat ttg aac aaa aca aat ttt aat cat tca gtg ttt gac gtg ccg ctt   1284
Tyr Leu Asn Lys Thr Asn Phe Asn His Ser Val Phe Asp Val Pro Leu
        275                 280                 285 cat tat cag ttc cat gct gca tcg aca cag gga ggc ggc tat gat atg   1332
His Tyr Gln Phe His Ala Ala Ser Thr Gln Gly Gly Gly Tyr Asp Met
    290                 295                 300 agg aaa ttg ctg aac ggt acg gtc gtt tcc aag cat ccg ttg aaa tcg   1380
Arg Lys Leu Leu Asn Gly Thr Val Val Ser Lys His Pro Leu Lys Ser
305                 310                 315                 320 gtt aca ttt gtc gat aac cat gat aca cag ccg ggg caa tcg ctt gag   1428
Val Thr Phe Val Asp Asn His Asp Thr Gln Pro Gly Gln Ser Leu Glu
                325                 330                 335 tcg act gtc caa aca tgg ttt aag ccg ctt gct tac gct ttt att ctc   1476
Ser Thr Val Gln Thr Trp Phe Lys Pro Leu Ala Tyr Ala Phe Ile Leu
            340                 345                 350 aca agg gaa tct gga tac cct cag gtt ttc tac ggg gat atg tac ggg   1524
Thr Arg Glu Ser Gly Tyr Pro Gln Val Phe Tyr Gly Asp Met Tyr Gly
        355                 360                 365 acg aaa gga gac tcc cag cgc gaa att cct gcc ttg aaa cac aaa att   1572
Thr Lys Gly Asp Ser Gln Arg Glu Ile Pro Ala Leu Lys His Lys Ile
    370                 375                 380 gaa ccg atc tta aaa gcg aga aaa cag tat gcg tac gga gca cag cat   1620
Glu Pro Ile Leu Lys Ala Arg Lys Gln Tyr Ala Tyr Gly Ala Gln His
385                 390                 395                 400 gat tat ttc gac cac cat gac att gtc ggc tgg aca agg gaa ggc gac   1668
Asp Tyr Phe Asp His His Asp Ile Val Gly Trp Thr Arg Glu Gly Asp
                405                 410                 415 agc tcg gtt gca aat tca ggt ttg gcg gca tta ata aca gac gga ccc   1716
Ser Ser Val Ala Asn Ser Gly Leu Ala Ala Leu Ile Thr Asp Gly Pro
            420                 425                 430 ggt ggg gca aag cga atg tat gtc ggc cgg caa aac gcc ggt gag aca   1764
Gly Gly Ala Lys Arg Met Tyr Val Gly Arg Gln Asn Ala Gly Glu Thr
        435                 440                 445 tgg cat gac att acc gga aac cgt tcg gag ccg gtt gtc atc aat tcg   1812
Trp His Asp Ile Thr Gly Asn Arg Ser Glu Pro Val Val Ile Asn Ser
    450                 455                 460
```

-continued

```
gaa ggc tgg gga gag ttt cac gta aac ggc ggg tcg gtt tca att tat    1860
Glu Gly Trp Gly Glu Phe His Val Asn Gly Gly Ser Val Ser Ile Tyr
465                 470                 475                 480 gtt caa aga tag aagagcagag aggacggatt tcctgaagga aatccgtttt        1912
Val Gln Arg * tttatttt                                                          1920

<210> SEQ ID NO 4
<211> LENGTH: 483
<212> TYPE: PRT
<213> ORGANISM: Bacillus licheniformis

<400> SEQUENCE: 4

Ala Asn Leu Asn Gly Thr Leu Met Gln Tyr Phe Glu Trp Tyr Met Pro
 1               5                  10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335
```

```
Ser Thr Val Gln Thr Trp Phe Lys Pro Leu Ala Tyr Ala Phe Ile Leu
        340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
        370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
        420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
        450                 455                 460

Glu Gly Trp Gly Glu Phe His Val Asn Gly Gly Ser Val Ser Ile Tyr
465                 470                 475                 480

Val Gln Arg

<210> SEQ ID NO 5
<211> LENGTH: 2604
<212> TYPE: DNA
<213> ORGANISM: Bacillus amyloliquefaciens

<400> SEQUENCE: 5
aagcttcaag cggtcaatcg gaatgtgcat ctcgcttcat acttaggttt tcacccgcat      60
attaagcagg cgttttttgaa ccgtgtgaca gaagctgttc gaaaccccgg cgggcggttt    120
gattttaagg ggggacagta tgctgcctct tcacattaat ctcagcggaa aagaatcat     180 cattgctggc gggggcaatg ttgcattaag aaggctgaaa cggtgtttcc ggaaggcgct    240
gatattaccg tgatcagtct gagcctgcct gaaattaaaa agctggcgga tgaaggacgc    300
atccgctgga ttccccggag aattgaaatg aaagatctca agcccgcttt tttcattatt    360
gccgcgacaa atgaccgagg cgtgaatcag agatagccg caaacgcttc tgaaacgcag    420
ctggtcaact gtgtaagcaa ggctgaacaa ggcagcgtat atatgccgaa gatcatccgc    480
aaagggcgca ttcaagtatc agtatcaaca agcggggcaa gccccgcaca tacgaaaaga    540
ctggctgaaa acattgagcc tttgatgact gatgatttgg ctgaagaagt ggatcgattg    600
tttgagaaaa gaagaagacc ataaaaatac cttgtctgtc atcagacagg gtattttta    660 tgctgtccag actgtccgct gtgtaaaaaa taggaataaa gggggttgt tattatttta    720 ctgatatgta aaatataatt tgtataagaa aatgagaggg agaggaaaca tgattcaaaa    780
acgaaagcgg acagtttcgt tcagacttgt gcttatgtgc acgctgttat ttgtcagttt    840
gccgattaca aaaacatcag ccgtaaatgg cacgctgatg cagtattttg aatggtatac    900
gccgaacgac ggccagcatt ggaaacgatt gcagaatgat gcgaacatt tatcggatat     960 cggaatcact gccgtctgga ttcctcccgc atacaaagga ttgagccaat ccgataacgg   1020 ataccggacct tatgatttgt atgatttagg agaattccag caaaagggga cggtcagaac   1080
gaaatacggc acaaatcag agcttcaaga tgcgatcggc tcactgcatt cccggaacgt   1140
ccaagtatac ggagatgtgg ttttgaatca taaggctggt gctgatgcaa cagaagatgt   1200
aactgccgtc gaagtcaatc cggccaatag aaatcaggaa acttcggagg aatatcaaat   1260
```

```
caaagcgtgg acggattttc gttttccggg ccgtggaaac acgtacagtg attttaaatg   1320
gcattggtat catttcgacg gagcggactg ggatgaatcc cggaagatca gccgcatctt   1380
taagtttcgt ggggaaggaa aagcgtggga ttgggaagta tcaagtgaaa acggcaacta   1440
tgactattta atgtatgctg atgttgacta cgaccaccct gatgtcgtgg cagagacaaa   1500
aaaatggggg atctggtatg cgaatgaact gtcattagac ggcttccgta ttgatgccgc   1560
caaacatatt aaattttcat ttctgcgtga ttgggttcag gcggtcagac aggcgacggg   1620
aaaagaaatg tttacggttg cggagtattg cagaataat gccgggaaac tcgaaaacta   1680
cttgaataaa acaagcttta atcaatccgt gtttgatgtt ccgcttcatt tcaatttaca   1740
ggcggcttcc tcacaaggag gcggatatga tatgaggcgt ttgctggacg gtaccgttgt   1800
gtccaggcat ccggaaaagg cggttacatt tgttgaaaat catgacacac agccgggaca   1860
gtcattggaa tcgacagtcc aaacttggtt taaaccgctt gcatacgcct ttattttgac   1920
aagagaatcc ggttatcctc aggtgttcta tggggatatg tacgggacaa aagggacatc   1980
gccaaaggaa attccctcac tgaaagataa tatagagccg atttaaaag cgcgtaagga   2040 gtacgcatac gggcccagc acgattatat tgaccacccg gatgtgatcg gatggacgag   2100
ggaaggtgac agctccgccg ccaaatcagg tttggccgct ttaatcacgg acggacccgg   2160
cggatcaaag cggatgtatg ccggcctgaa aaatgccggc gagacatggt atgacataac   2220
gggcaaccgt tcagatactg taaaaatcgg atctgacggc tggggagagt ttcatgtaaa   2280
cgatgggtcc gtctccattt atgttcagaa ataaggtaat aaaaaaacac ctccaagctg   2340
agtgcgggta tcagcttgga ggtgcgttta ttttttcagc cgtatgacaa ggtcggcatc   2400
aggtgtgaca aatacggtat gctggctgtc ataggtgaca aatccgggtt ttgcgccgtt   2460 tggcttttc acatgtctga tttttgtata atcaacaggc acggagccgg aatctttcgc   2520
cttgaaaaaa taagcggcga tcgtagctgc ttccaatatg gattgttcat cgggatcgct   2580
gcttttaatc acaacgtggg atcc                                         2604
```

<210> SEQ ID NO 6
<211> LENGTH: 483
<212> TYPE: PRT
<213> ORGANISM: Bacillus amyloliquefaciens

<400> SEQUENCE: 6

```
Val Asn Gly Thr Leu Met Gln Tyr Phe Glu Trp Tyr Thr Pro Asn Asp
 1               5                  10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125
```

```
Glu Glu Tyr Gln Ile Lys Ala Trp Thr Asp Phe Arg Phe Pro Gly Arg
    130                 135                 140
Gly Asn Thr Tyr Ser Asp Phe Lys Trp His Trp Tyr His Phe Asp Gly
145                 150                 155                 160
Ala Asp Trp Asp Glu Ser Arg Lys Ile Ser Arg Ile Phe Lys Phe Arg
                165                 170                 175
Gly Glu Gly Lys Ala Trp Asp Trp Glu Val Ser Ser Glu Asn Gly Asn
            180                 185                 190
Tyr Asp Tyr Leu Met Tyr Ala Asp Val Asp Tyr Asp His Pro Asp Val
        195                 200                 205
Val Ala Glu Thr Lys Lys Trp Gly Ile Trp Tyr Ala Asn Glu Leu Ser
    210                 215                 220
Leu Asp Gly Phe Arg Ile Asp Ala Ala Lys His Ile Lys Phe Ser Phe
225                 230                 235                 240
Leu Arg Asp Trp Val Gln Ala Val Arg Gln Ala Thr Gly Lys Glu Met
                245                 250                 255
Phe Thr Val Ala Glu Tyr Trp Gln Asn Asn Ala Gly Lys Leu Glu Asn
            260                 265                 270
Tyr Leu Asn Lys Thr Ser Phe Asn Gln Ser Val Phe Asp Val Pro Leu
        275                 280                 285
His Phe Asn Leu Gln Ala Ala Ser Ser Gln Gly Gly Tyr Asp Met
    290                 295                 300
Arg Arg Leu Leu Asp Gly Thr Val Val Ser Arg His Pro Glu Lys Ala
305                 310                 315                 320
Val Thr Phe Val Glu Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
            340                 345                 350
Thr Arg Glu Ser Gly Tyr Pro Gln Val Phe Tyr Gly Asp Met Tyr Gly
        355                 360                 365
Thr Lys Gly Thr Ser Pro Lys Glu Ile Pro Ser Leu Lys Asp Asn Ile
    370                 375                 380
Glu Pro Ile Leu Lys Ala Arg Lys Glu Tyr Ala Tyr Gly Pro Gln His
385                 390                 395                 400
Asp Tyr Ile Asp His Pro Asp Val Ile Gly Trp Thr Arg Glu Gly Asp
                405                 410                 415
Ser Ser Ala Ala Lys Ser Gly Leu Ala Ala Leu Ile Thr Asp Gly Pro
            420                 425                 430
Gly Gly Ser Lys Arg Met Tyr Ala Gly Leu Lys Asn Ala Gly Glu Thr
        435                 440                 445
Trp Tyr Asp Ile Thr Gly Asn Arg Ser Asp Thr Val Lys Ile Gly Ser
    450                 455                 460
Asp Gly Trp Gly Glu Phe His Val Asn Asp Gly Ser Val Ser Ile Tyr
465                 470                 475                 480
Val Gln Lys
```

<210> SEQ ID NO 7
<211> LENGTH: 1548
<212> TYPE: DNA
<213> ORGANISM: Bacillus stearothermophilus
<220> FEATURE:
<221> NAME/KEY: CDS
<222> LOCATION: (1)...(1548)

<400> SEQUENCE: 7

```
gcc gca ccg ttt aac ggc acc atg atg cag tat ttt gaa tgg tac ttg      48
Ala Ala Pro Phe Asn Gly Thr Met Met Gln Tyr Phe Glu Trp Tyr Leu
 1               5                  10                  15 ccg gat gat ggc acg tta tgg acc aaa gtg gcc aat gaa gcc aac aac      96
Pro Asp Asp Gly Thr Leu Trp Thr Lys Val Ala Asn Glu Ala Asn Asn
             20                  25                  30 tta tcc agc ctt ggc atc acc gct ctt tgg ctg ccg ccc gct tac aaa     144
Leu Ser Ser Leu Gly Ile Thr Ala Leu Trp Leu Pro Pro Ala Tyr Lys
         35                  40                  45 gga aca agc cgc agc gac gta ggg tac gga gta tac gac ttg tat gac     192
Gly Thr Ser Arg Ser Asp Val Gly Tyr Gly Val Tyr Asp Leu Tyr Asp
     50                  55                  60 ctc ggc gaa ttc aat caa aaa ggg acc gtc cgc aca aaa tac gga aca     240
Leu Gly Glu Phe Asn Gln Lys Gly Thr Val Arg Thr Lys Tyr Gly Thr
 65                  70                  75                  80 aaa gct caa tat ctt caa gcc att caa gcc gcc cac gcc gct gga atg     288
Lys Ala Gln Tyr Leu Gln Ala Ile Gln Ala Ala His Ala Ala Gly Met
                 85                  90                  95 caa gtg tac gcc gat gtc gtg ttc gac cat aaa ggc ggc gct gac ggc     336
Gln Val Tyr Ala Asp Val Val Phe Asp His Lys Gly Gly Ala Asp Gly
            100                 105                 110 acg gaa tgg gtg gac gcc gtc gaa gtc aat ccg tcc gac cgc aac caa     384
Thr Glu Trp Val Asp Ala Val Glu Val Asn Pro Ser Asp Arg Asn Gln
        115                 120                 125 gaa atc tcg ggc acc tat caa atc caa gca tgg acg aaa ttt gat ttt     432
Glu Ile Ser Gly Thr Tyr Gln Ile Gln Ala Trp Thr Lys Phe Asp Phe
    130                 135                 140 ccc ggg cgg ggc aac acc tac tcc agc ttt aag tgg cgc tgg tac cat     480
Pro Gly Arg Gly Asn Thr Tyr Ser Ser Phe Lys Trp Arg Trp Tyr His
145                 150                 155                 160 ttt gac ggc gtt gat tgg gac gaa agc cga aaa ttg agc cgc att tac     528
Phe Asp Gly Val Asp Trp Asp Glu Ser Arg Lys Leu Ser Arg Ile Tyr
                165                 170                 175 aaa ttc cgc ggc atc ggc aaa gcg tgg gat tgg gaa gta gac acg gaa     576
Lys Phe Arg Gly Ile Gly Lys Ala Trp Asp Trp Glu Val Asp Thr Glu
            180                 185                 190 aac gga aac tat gac tac tta atg tat gcc gac ctt gat atg gat cat     624
Asn Gly Asn Tyr Asp Tyr Leu Met Tyr Ala Asp Leu Asp Met Asp His
        195                 200                 205 ccc gaa gtc gtg acc gag ctg aaa aac tgg ggg aaa tgg tat gtc aac     672
Pro Glu Val Val Thr Glu Leu Lys Asn Trp Gly Lys Trp Tyr Val Asn
    210                 215                 220 aca acg aac att gat ggg ttc cgg ctt gat gcc gtc aag cat att aag     720
Thr Thr Asn Ile Asp Gly Phe Arg Leu Asp Ala Val Lys His Ile Lys
225                 230                 235                 240 ttc agt ttt ttt cct gat tgg ttg tcg tat gtg cgt tct cag act ggc     768
Phe Ser Phe Phe Pro Asp Trp Leu Ser Tyr Val Arg Ser Gln Thr Gly
                245                 250                 255 aag ccg cta ttt acc gtc ggg gaa tat tgg agc tat gac atc aac aag     816
Lys Pro Leu Phe Thr Val Gly Glu Tyr Trp Ser Tyr Asp Ile Asn Lys
            260                 265                 270 ttg cac aat tac att acg aaa aca gac gga acg atg tct ttg ttt gat     864
Leu His Asn Tyr Ile Thr Lys Thr Asp Gly Thr Met Ser Leu Phe Asp
        275                 280                 285 gcc ccg tta cac aac aaa ttt tat acc gct tcc aaa tca ggg ggc gca     912
Ala Pro Leu His Asn Lys Phe Tyr Thr Ala Ser Lys Ser Gly Gly Ala
    290                 295                 300 ttt gat atg cgc acg tta atg acc aat act ctc atg aaa gat caa ccg     960
Phe Asp Met Arg Thr Leu Met Thr Asn Thr Leu Met Lys Asp Gln Pro
305                 310                 315                 320
```

```
aca ttg gcc gtc acc ttc gtt gat aat cat gac acc gaa ccc ggc caa    1008
Thr Leu Ala Val Thr Phe Val Asp Asn His Asp Thr Glu Pro Gly Gln
            325                 330                 335 gcg ctg cag tca tgg gtc gac cca tgg ttc aaa ccg ttg gct tac gcc    1056
Ala Leu Gln Ser Trp Val Asp Pro Trp Phe Lys Pro Leu Ala Tyr Ala
            340                 345                 350 ttt att cta act cgg cag gaa gga tac ccg tgc gtc ttt tat ggt gac    1104
Phe Ile Leu Thr Arg Gln Glu Gly Tyr Pro Cys Val Phe Tyr Gly Asp
            355                 360                 365 tat tat ggc att cca caa tat aac att cct tcg ctg aaa agc aaa atc    1152
Tyr Tyr Gly Ile Pro Gln Tyr Asn Ile Pro Ser Leu Lys Ser Lys Ile
        370                 375                 380 gat ccg ctc ctc atc gcg cgc agg gat tat gct tac gga acg caa cat    1200
Asp Pro Leu Leu Ile Ala Arg Arg Asp Tyr Ala Tyr Gly Thr Gln His
385                 390                 395                 400 gat tat ctt gat cac tcc gac atc atc ggg tgg aca agg gaa ggg ggc    1248
Asp Tyr Leu Asp His Ser Asp Ile Ile Gly Trp Thr Arg Glu Gly Gly
                405                 410                 415 act gaa aaa cca gga tcc gga ctg gcc gca ctg atc acc gat ggg ccg    1296
Thr Glu Lys Pro Gly Ser Gly Leu Ala Ala Leu Ile Thr Asp Gly Pro
                420                 425                 430 gga gga agc aaa tgg atg tac gtt ggc aaa caa cac gct gga aaa gtg    1344
Gly Gly Ser Lys Trp Met Tyr Val Gly Lys Gln His Ala Gly Lys Val
                435                 440                 445 ttc tat gac ctt acc ggc aac cgg agt gac acc gtc acc atc aac agt    1392
Phe Tyr Asp Leu Thr Gly Asn Arg Ser Asp Thr Val Thr Ile Asn Ser
        450                 455                 460 gat gga tgg ggg gaa ttc aaa gtc aat ggc ggt tcg gtt tcg gtt tgg    1440
Asp Gly Trp Gly Glu Phe Lys Val Asn Gly Gly Ser Val Ser Val Trp
465                 470                 475                 480 gtt cct aga aaa acg acc gtt tct acc atc gct cgg ccg atc aca acc    1488
Val Pro Arg Lys Thr Thr Val Ser Thr Ile Ala Arg Pro Ile Thr Thr
                485                 490                 495 cga ccg tgg act ggt gaa ttc gtc cgt tgg acc gaa cca cgg ttg gtg    1536
Arg Pro Trp Thr Gly Glu Phe Val Arg Trp Thr Glu Pro Arg Leu Val
            500                 505                 510 gca tgg cct tga                                                    1548
Ala Trp Pro *
        515

<210> SEQ ID NO 8
<211> LENGTH: 515
<212> TYPE: PRT
<213> ORGANISM: Bacillus stearothermophilus

<400> SEQUENCE: 8

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95
```

```
Gln Val Tyr Ala Asp Val Val Phe Asp His Lys Gly Ala Asp Gly
            100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
            130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
            210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asp Gly Thr Met Ser Leu Phe Asp
            275                 280                 285

Ala Pro Leu His Asn Lys Phe Tyr Thr Ala Ser Lys Ser Gly Gly Ala
            290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
            370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Gly
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
            450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
```

515

<210> SEQ ID NO 9
<211> LENGTH: 31
<212> TYPE: DNA
<213> ORGANISM: Artificial Sequence
<220> FEATURE:
<223> OTHER INFORMATION: Primer

<400> SEQUENCE: 9
ggtcgtaggc accgtagccc caatccgctt g                           31

<210> SEQ ID NO 10
<211> LENGTH: 36
<212> TYPE: DNA
<213> ORGANISM: Artificial Sequence
<220> FEATURE:
<223> OTHER INFORMATION: Primer

<400> SEQUENCE: 10
ggtcgtaggc accgtagccc caatcccatt ggctcg                      36

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
ctgtgactgg tgagtactca accaagtc                               28

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
ggtcgtaggc accgtagccc tcatccgctt g                           31

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
ggtcgtaggc accgtagccc atatccgctt g                           31

<210> SEQ ID NO 14
<211> LENGTH: 31
<212> TYPE: DNA
<213> ORGANISM: Artificial Sequence
<220> FEATURE:
<223> OTHER INFORMATION: Primer

<400> SEQUENCE: 14
ggtcgtaggc accgtagcca atatccgctt g                           31

<210> SEQ ID NO 15
<211> LENGTH: 36
<212> TYPE: DNA
<213> ORGANISM: Artificial Sequence

```
<220> FEATURE:
<223> OTHER INFORMATION: Primer

<400> SEQUENCE: 15
gcagcatgga actgctyatg aagaggcacg tcaaac                              36

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
catagttgcc gaattcattg gaaacttccc                                     30

<210> SEQ ID NO 17
<211> LENGTH: 34
<212> TYPE: DNA
<213> ORGANISM: Artificial Sequence
<220> FEATURE:
<223> OTHER INFORMATION: Primer

<400> SEQUENCE: 17
catagttgcc gaattcaggg gaaacttccc aatc                                34

<210> SEQ ID NO 18
<211> LENGTH: 41
<212> TYPE: DNA
<213> ORGANISM: Artificial Sequence
<220> FEATURE:
<223> OTHER INFORMATION: Primer

<400> SEQUENCE: 18
ccgcgccccg ggaaatcaaa ttttgtccag gctttaatta g                        41

<210> SEQ ID NO 19
<211> LENGTH: 32
<212> TYPE: DNA
<213> ORGANISM: Artificial Sequence
<220> FEATURE:
<223> OTHER INFORMATION: Primer

<400> SEQUENCE: 19
caaaatggta ccaataccac ttaaaatcgc tg                                  32

<210> SEQ ID NO 20
<211> LENGTH: 29
<212> TYPE: DNA
<213> ORGANISM: Artificial Sequence
<220> FEATURE:
<223> OTHER INFORMATION: Primer

<400> SEQUENCE: 20
cttcccaatc ccaagtcttc ccttgaaac                                      29

<210> SEQ ID NO 21
<211> LENGTH: 36
<212> TYPE: DNA
<213> ORGANISM: Artificial Sequence
<220> FEATURE:
<223> OTHER INFORMATION: Primer

<400> SEQUENCE: 21
cttaatttct gctacgacgt caggatggtc ataatc                              36
```

```
<210> SEQ ID NO 22
<211> LENGTH: 38
<212> TYPE: DNA
<213> ORGANISM: Artificial Sequence
<220> FEATURE:
<223> OTHER INFORMATION: Primer

<400> SEQUENCE: 22
cgcccaagtc attcgaccag tactcagcta ccgtaaac                              38

<210> SEQ ID NO 23
<211> LENGTH: 29
<212> TYPE: DNA
<213> ORGANISM: Artificial Sequence
<220> FEATURE:
<223> OTHER INFORMATION: Primer

<400> SEQUENCE: 23
gccgttttca ttgtcgactt cccaatccc                                       29

<210> SEQ ID NO 24
<211> LENGTH: 35
<212> TYPE: DNA
<213> ORGANISM: Artificial Sequence
<220> FEATURE:
<223> OTHER INFORMATION: Primer

<400> SEQUENCE: 24
ggaatttcgc gctgactagt cccgtacata tcccc                                35

<210> SEQ ID NO 25
<211> LENGTH: 36
<212> TYPE: DNA
<213> ORGANISM: Artificial Sequence
<220> FEATURE:
<223> OTHER INFORMATION: Primer

<400> SEQUENCE: 25
ggcaggaatt tcgcgacctt tcgtcccgta catatc                               36

<210> SEQ ID NO 26
<211> LENGTH: 36
<212> TYPE: DNA
<213> ORGANISM: Artificial Sequence
<220> FEATURE:
<223> OTHER INFORMATION: Primer

<400> SEQUENCE: 26
cctcattctg cagcagcagc cgtaaatggc acgctg                               36

<210> SEQ ID NO 27
<211> LENGTH: 38
<212> TYPE: DNA
<213> ORGANISM: Artificial Sequence
<220> FEATURE:
<223> OTHER INFORMATION: Primer

<400> SEQUENCE: 27
ccagacggca gtaataccga tatccgataa atgttccg                             38

<210> SEQ ID NO 28
<211> LENGTH: 30
<212> TYPE: DNA
<213> ORGANISM: Artificial Sequence
<220> FEATURE:
<223> OTHER INFORMATION: Primer
```

```
<400> SEQUENCE: 28
cggatatcgg tattactgcc gtctggattc                                30

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
ctcgtcccaa tcggttccgt c                                         21

<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
gatgtatgcc gacttcgatt atgacc                                    26

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
catagttgcc gaattcattg gaaacttccc                                30

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
ccgattgctg acgctgttat ttgc                                      24

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
gccaagcgga taacggctac ggtgc                                     25

<210> SEQ ID NO 34
<211> LENGTH: 28
<212> TYPE: DNA
<213> ORGANISM: Artificial Sequence
<220> FEATURE:
<223> OTHER INFORMATION: Primer

<400> SEQUENCE: 34
gaacgagcca atcggacgtg ggctacgg                                  28

<210> SEQ ID NO 35
```

```
<211> LENGTH: 32
<212> TYPE: DNA
<213> ORGANISM: Artificial Sequence
<220> FEATURE:
<223> OTHER INFORMATION: Primer

<400> SEQUENCE: 35
ggaacgagcc aatcggataa cggctacggt gc                                   32

<210> SEQ ID NO 36
<211> LENGTH: 25
<212> TYPE: DNA
<213> ORGANISM: Artificial Sequence
<220> FEATURE:
<223> OTHER INFORMATION: Primer

<400> SEQUENCE: 36
gcatataagg gactgagcca agcgg                                           25

<210> SEQ ID NO 37
<211> LENGTH: 25
<212> TYPE: DNA
<213> ORGANISM: Artificial Sequence
<220> FEATURE:
<223> OTHER INFORMATION: Primer

<400> SEQUENCE: 37
caaccacaaa gccggcgctg atgcg                                           25

<210> SEQ ID NO 38
<211> LENGTH: 41
<212> TYPE: DNA
<213> ORGANISM: Artificial Sequence
<220> FEATURE:
<223> OTHER INFORMATION: Primer

<400> SEQUENCE: 38
gcatataagg gactgagcca atcggataac ggctacggtg c                         41

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
gaacgagccg atcggacgtg ggctacgg                                        28

<210> SEQ ID NO 40
<211> LENGTH: 28
<212> TYPE: DNA
<213> ORGANISM: Artificial Sequence
<220> FEATURE:
<223> OTHER INFORMATION: Primer

<400> SEQUENCE: 40
gaacgagcca aaacgacgtg ggctacgg                                        28
```

ALPHA-AMYLASE VARIANTS

CROSS-REFERENCE TO RELATED APPLICATIONS

This application is a division of U.S. application Ser. No. 10/146,327 (now U.S. Pat. No. 7,306,936), filed on May 15, 2002, which is a division of U.S. application Ser. No. 09/537,168 (now U.S. Pat. No. 6,410,295), filed Mar. 29, 2000, and claims, under 35 U.S.C. 119, priority of Danish application no. PA 1999 00437 filed Mar. 30, 1999, and claims the benefit of US provisional No. 60/127,427 filed on Apr. 1, 1999, the contents of which are fully incorporated herein by reference.

FIELD OF THE INVENTION

The present invention relates, inter alia, to novel variants of parent Termamyl-like alpha-amylases, notably variants exhibiting altered properties, in particular altered cleavage pattern (relative to the parent) which are advantageous with respect to applications of the variants in, in particular, industrial starch processing (e.g., starch liquefaction or saccharification).

BACKGROUND OF THE INVENTION

Alpha-Amylases (alpha-1,4-glucan-4-glucanohydrolases, EC 3.2.1.1) constitute a group of enzymes which catalyze hydrolysis of starch and other linear and branched 1,4-glucosidic oligo- and polysaccharides.

There is a very extensive body of patent and scientific literature relating to this industrially very important class of enzymes. A number of alpha-amylase such as Termamyl-like alpha-amylases variants are known from, e.g., WO 90/11352, WO 95/10603, WO 95/26397, WO 96/23373, WO 96/23874 and WO 97/41213.

Among recent disclosure relating to alpha-amylases, WO 96/23874 provides three-dimensional, X-ray crystal structural data for a Termamyl-like alpha-amylase, referred to as BA2, which consists of the 300 N-terminal amino acid residues of the *B. amyloliquefaciens* alpha-amylase comprising the amino acid sequence shown in SEQ ID NO: 6 herein and amino acids 301-483 of the C-terminal end of the *B. licheniformis* alpha-amylase comprising the amino acid sequence shown in SEQ ID NO: 4 herein (the latter being available commercially under the tradename Termamyl™), and which is thus closely related to the industrially important *Bacillus* alpha-amylases (which in the present context are embraced within the meaning of the term "Termamyl-like alpha-amylases", and which include, inter alia, the *B. licheniformis, B. amyloliquefaciens* and *B. stearothermophilus* alpha-amylases). WO 96/23874 further describes methodology for designing, on the basis of an analysis of the structure of a parent Termamyl-like alpha-amylase, variants of the parent Termamyl-like alpha-amylase which exhibit altered properties relative to the parent.

WO 96/23874 and WO 97/41213 (Novo Nordisk) discloses Termamyl-like alpha-amylase variants with an altered cleavage pattern containing mutations in the amino acid residues V54, D53, Y56, Q333, G57 and A52 of the sequence shown in SEQ ID NO: 4 herein.

BRIEF DISCLOSURE OF THE INVENTION

The present invention relates to novel alpha-amylolytic variants (mutants) of a Termamyl-like alpha-amylase, in particular variants exhibiting altered cleavage pattern (relative to the parent), which are advantageous in connection with the industrial processing of starch (starch liquefaction, saccharification and the like).

The inventors have surprisingly found variants with altered properties, in particular altered cleavage pattern which have improved reduced capability of cleaving an substrate close to the branching point, and further have improved substrate specificity and/or improved specific activity, in comparison to the WO 96/23874 and WO 97/41213 (Novo Nordisk) disclosed Termamyl-like alpha-amylase variants with an altered cleavage pattern containing mutations in the amino acid residues V54, D53, Y56, Q333, G57 and A52 of the sequence shown in SEQ ID NO: 4 herein.

The invention further relates to DNA constructs encoding variants of the invention, to composition comprising variants of the invention, to methods for preparing variants or the invention, and to the use of variants and compositions of the invention, alone or in combination with other alpha-amylolytic enzymes, in various industrial processes, e.g., starch liquefaction, and in detergent compositions, such as laundry, dish washing and hard surface cleaning compositions; ethanol production, such as fuel, drinking and industrial ethanol production; desiring of textiles, fabrics or garments etc.

Nomenclature

In the present description and claims, the conventional one-letter and three-letter codes for amino acid residues are used. For ease of reference, alpha-amylase variants of the invention are described by use of the following nomenclature:

Original amino acid(s):position(s):substituted amino acid(s)

According to this nomenclature, for instance the substitution of alanine for asparagine in position 30 is shown as:
   Ala30Asn or A30N a deletion of alanine in the same position is shown as:
   Ala30* or A30* and insertion of an additional amino acid residue, such as lysine, is shown as:
   *30aLys or *30aK A deletion of a consecutive stretch of amino acid residues, such as amino acid residues 30-33, is indicated as (30-33)* or Δ(A30-N33) or delta (A30-N33).

Where a specific alpha-amylase contains a "deletion" in comparison with other alpha-amylases and an insertion is made in such a position this is indicated as:
   *36aAsp or *36aD for insertion of an aspartic acid in position 36

Multiple mutations are separated by plus signs, i.e.:
   Ala30Asp+Glu34Ser or A30N+E34S representing mutations in positions 30 and 34 substituting alanine and glutamic acid for asparagine and serine, respectively. Multiple mutations may also be separated as follows, i.e., meaning the same as the plus sign:
   Ala30Asp/Glu34Ser or A30N/E34S When one or more alternative amino acid residues may be inserted in a given position it is indicated as
   A30N, E or
   A30N or A30E Furthermore, when a position suitable for modification is identified herein without any specific modification being suggested, or A30X, it is to be understood that any amino acid residue may be substituted for the amino acid residue present in the position. Thus, for instance, when a modification of an alanine in position 30 is mentioned, but not specified, or specified as "X", it is to be understood that the alanine may be deleted or substituted for any other amino acid, i.e., any one of: R, N, D, C, Q, E, G, H, I, L, K, M, F, P, S, T, W, Y, V.

DETAILED DISCLOSURE OF THE INVENTION

The Termamyl-Like Alpha-Amylase

It is well known that a number of alpha-amylases produced by Bacillus spp. are highly homologous on the amino acid level. For instance, the B. licheniformis alpha-amylase comprising the amino acid sequence shown in SEQ ID NO: 4 (commercially available as Termamyl™) has been found to be about 89% homologous with the B. amyloliquefaciens alpha-amylase comprising the amino acid sequence shown in SEQ ID NO: 6 and about 79% homologous with the B. stearothermophilus alpha-amylase comprising the amino acid sequence shown in SEQ ID NO: 8. Further homologous alpha-amylases include an alpha-amylase derived from a strain of the Bacillus sp. NCIB 12289, NCIB 12512, NCIB 12513 or DSM 9375, all of which are described in detail in WO 95/26397, and the #707 alpha-amylase described by Tsukamoto et al., Biochemical and Biophysical Research Communications, 151 (1988), pp. 25-31.

Still further homologous alpha-amylases include the alpha-amylase produced by the B. licheniformis strain described in EP 0252666 (ATCC 27811), and the alpha-amylases identified in WO 91/00353 and WO 94/18314. Other commercial Termamyl-like B. licheniformis alpha-amylases are Optitherm™ and Takatherm™ (available from Solvay), Maxamyl™ (available from Gist-brocades/Genencor), Spezym AA™ and Spesyme Delta AA™ (available from Genencor), and Keistase™ (available from Daiwa).

Because of the substantial homology found between these alpha-amylases, they are considered to belong to the same class of alpha-amylases, namely the class of "Termamyl-like alpha-amylases".

Accordingly, in the present context, the term "Termamyl-like alpha-amylase" is intended to indicate an alpha-amylase, which at the amino acid level exhibits a substantial homology to Termamyl™, i.e., the B. licheniformis alpha-amylase having the amino acid sequence shown, in SEQ ID NO: 4 herein. In other words, a Termamyl-like alpha-amylase is an alpha-amylase, which has the amino acid sequence shown in SEQ ID NO: 2, 4, 6, or 8 herein, and the amino acid sequence shown in SEQ ID NO: 1 or 2 of WO 95/26397 or in Tsukamoto et al., 1988, or i) which displays at least 60%, preferred at least 70%, more preferred at least 75%, even more preferred at least 80%, especially at least 85%, especially preferred at least 90%, even especially more preferred at least 95% homology, more preferred at least 97%, more preferred at least 99% with at least one of said amino acid sequences and/or ii) displays immunological cross-reactivity with an antibody raised against at least one of said alpha-amylases, and/or iii) is encoded by a DNA sequence which hybridises to the DNA sequences encoding the above-specified alpha-amylases which are apparent from SEQ ID NOS: 1, 3, 5 and 7 of the present application and SEQ ID NOS: 4 and 5 of WO 95/26397, respectively.

In connection with property i), the "homology" may be determined by use of any conventional algorithm, preferably by use of the GAP progamme from the GCG package version 7.3 (June 1993) using default values for GAP penalties, which is a GAP creation penalty of 3.0 and GAP extension penalty of 0.1, (Genetic Computer Group (1991) Programme Manual for the GCG Package, version 7, 575 Science Drive, Madison, Wis., USA 53711).

A structural alignment between Termamyl and a Termamyl-like alpha-amylase may be used to identify equivalent/corresponding positions in other Termamyl-like alpha-amylases. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., (1987), FEES LETTERS 224, pp. 149-155) and reverse threading (Huber, T; Torda, A E, PROTEIN SCIENCE Vol. 7, No. 1 pp. 142-149 (1998). Property ii) of the alpha-amylase, i.e., the immunological cross reactivity, may be assayed using an antibody raised against, or reactive with, at least one epitope of the relevant Termamyl-like alpha-amylase. The antibody, which may either be monoclonal or polyclonal, may be produced by methods known in the art, e.g., as described by Hudson et al., Practical Immunology, Third edition (1989), Blackwell Scientific Publications. The immunological cross-reactivity may be determined using assays known in the art, examples of which are Western Blotting or radial immunodiffusion assay, e.g., as described by Hudson et al., 1989. In this respect, immunological cross-reactivity between the alpha-amylases having the amino acid sequences SEQ ID NOS: 2, 4, 6, or 8, respectively, have been found.

The oligonucleotide probe used in the characterization of the Termamyl-like alpha-amylase in accordance with property iii) above may suitably be prepared on the basis of the full or partial nucleotide or amino acid sequence of the alpha-amylase in question.

Suitable conditions for testing hybridization involve presoaking in 5×SSC and prehybridizing for 1 hour at ~40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at ~40° C., followed by three times washing of the filter in 2×SSC, 0.2% SDS at 40° C. for 30 minutes (low stringency), preferred at 50° C. (medium stringency), more preferably at 65° C. (high stringency), even more preferably at ~75° C. (very high stringency). More details about the hybridization method can be found in Sambrook et al., Molecular Cloning: A Laboratory Manual, 2nd Ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase, which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e. a variant, which is the result of a modification (insertion, substitution, deletion) of one or more amino acid residues of the naturally occurring alpha-amylase.

Parent Hybrid Alpha-Amylases

The parent alpha-amylase may be a hybrid alpha-amylase, i.e., an alpha-amylase, which comprises a combination of partial amino acid sequences derived from at least two alpha-amylases.

The parent hybrid alpha-amylase may be one, which on the basis of amino acid homology and/or immunological cross-reactivity and/or DNA hybridization (as defined above) can be determined to belong to the Termamyl-like alpha-amylase family. In this case, the hybrid alpha-amylase is typically composed of at least one part of a Termamyl-like alpha-amylase and part(s) of one or more other alpha-amylases selected from Termamyl-like alpha-amylases or non-Termamyl-like alpha-amylases of microbial (bacterial or fungal) and/or mammalian origin.

Thus, the parent hybrid alpha-amylase may comprise a combination of partial amino acid sequences deriving from at least two Termamyl-like alpha-amylases, or from at least one Termamyl-like and at least one non-Termamyl-like bacterial alpha-amylase, or from at least one Termamyl-like and at least one fungal alpha-amylase. The Termamyl-like alpha-amylase from which a partial amino acid sequence derives may, e.g., be any of those specific Termamyl-like alpha-amylases referred to herein.

For instance, the parent alpha-amylase may comprise a C-terminal part of an alpha-amylase derived from a strain of *B. licheniformis*, and a N-terminal part of an alpha-amylase derived from a strain of *B. amyloliquefaciens* or from a strain of *B. stearothermophilus*. For instance, the parent alpha-amylase may comprise at least 430 amino acid residues of the C-terminal part of the *B. licheniformis* alpha-amylase, and may, e.g., comprise a) an amino acid segment corresponding to the 37 N-terminal amino acid residues of the *B. amyloliquefaciens* alpha-amylase having the amino acid sequence shown in SEQ ID NO: 6 and an amino acid segment corresponding to the 445 C-terminal amino acid residues of the *B. licheniformis* alpha-amylase having the amino acid sequence shown in SEQ ID NO: 4, or b) an amino acid segment corresponding to the 68 N-terminal amino acid residues of the *B. stearothermophilus* alpha-amylase having the amino acid sequence shown in SEQ ID NO: 8 and an amino acid segment corresponding to the 415 C-terminal amino acid residues of the *B. licheniformis* alpha-amylase having the amino acid sequence shown in SEQ ID NO: 4.

In a preferred embodiment the parent Termamyl-like alpha-amylase is a hybrid Termamyl-like alpha-amylase identical to the *Bacillus licheniformis* alpha-amylase shown in SEQ ID NO: 4, except that the N-terminal 35 amino acid residues (of the mature protein) is replaced with the N-terminal 33 amino acid residues of the mature protein of the *Bacillus amyloliquefaciens* alpha-amylase (BAN) shown in SEQ ID NO: 6. Said hybrid may further have the following mutations: H156Y+A181T+N190F+A209V+Q264S (using the numbering in SEQ ID NO: 4) referred to as LE174.

Another preferred parent hybrid alpha-amylase is LE429 shown in SEQ ID NO: 2.

The non-Termamyl-like alpha-amylase may, e.g., be a fungal alpha-amylase, a mammalian or a plant alpha-amylase or a bacterial alpha-amylase (different from a Termamyl-like alpha-amylase). Specific examples of such alpha-amylases include the *Aspergillus oryzae* TAKA alpha-amylase, the *A. niger* acid alpha-amylase, the *Bacillus subtilis* alpha-amylase, the porcine pancreatic alpha-amylase and a barley alpha-amylase. All of these alpha-amylases have elucidated structures, which are markedly different from the structure of a typical Termamyl-like alpha-amylase as referred to herein.

The fungal alpha-amylases mentioned above, i.e., derived from *A. niger* and *A. oryzae*, are highly homologous on the amino acid level and generally considered to belong to the same family of alpha-amylases. The fungal alpha-amylase derived from *Aspergillus oryzae* is commercially available under the tradename Fungamyl™.

Furthermore, when a particular variant of a Termamyl-like alpha-amylase (variant of the invention) is referred to—in a conventional manner—by reference to modification (e.g., deletion or substitution) of specific amino acid residues in the amino acid sequence of a specific Termamyl-like alpha-amylase, it is to be understood that variants of another Termamyl-like alpha-amylase modified in the equivalent position (s) (as determined from the best possible amino acid sequence alignment between the respective amino acid sequences) are encompassed thereby.

A preferred embodiment of a variant of the invention is one derived from a *B. licheniformis* alpha-amylase (as parent Termamyl-like alpha-amylase), e.g., one of those referred to above, such as the *B. licheniformis* alpha-amylase having the amino acid sequence shown in SEQ ID NO: 4.

Construction of Variants of the Invention

The construction of the variant of interest may be accomplished by cultivating a microorganism comprising a DNA sequence encoding the variant under conditions which are conducive for producing the variant. The variant may then subsequently be recovered from the resulting culture broth. This is described in detail further below.

Altered Properties

The following discusses the relationship between mutations, which may be present in variants of the invention, and desirable alterations in properties (relative to those of a parent Termamyl-like alpha-amylase), which may result there from.

In the first aspect the invention relates to a variant of a parent Termamyl-like alpha-amylase, comprising an alteration at one or more positions selected from the group of:

W13, G48, T49, S50, Q51, A52, D53, V54, G57, G107, G108, A111, S168, M197, wherein (a) the alteration (s) are independently (i) an insertion of an amino acid downstream of the amino acid which occupies the position, (ii) a deletion of the amino acid which occupies the position, or (iii) a substitution of the amino acid which occupies the position with a different amino acid, (b) the variant has alpha-amylase activity and (c) each position corresponds to a position of the amino acid sequence of the parent Termamyl-like alpha-amylase having the amino acid sequence of SEQ ID NO: 4.

In a preferred embodiment the above variants of the invention comprise a mutation in a position corresponding to at least one of the following mutations in the amino acid sequence shown in SEQ ID NO: 4:

V54N, A52S, A52S+V54N, T49L, T49+G107A, A52S+V54N+T49L+G107A, A52S+V54N+T49L, G107A, Q51R, Q51R+A52S, A52N; or

T49F+G107A, T49V+G107A, T49D+G107A, T49Y+G107A, T49S+G107A, T49N+G107A, T49I+G107A, T49L+A52S+G107A, T49L+A52T+G107A, T49L+A52F+G107A, T49L+A52L+G107A, T49L+A52I+G107A, T49L+A52V+G107A; or

T49V, T49I, T49D, T49N, T49S, T49Y, T49F, T49W, T49M, T49E, T49Q, T49K, T49R, A52T, A52L, A52I, A52V, A52M, A52F, A52Y, A52W, V54M, G107V, G07I, G107L, G107C.

In a preferred embodiment a variant of the invention comprises at least one mutation in a position corresponding to the following mutations in the amino acid sequence shown in SEQ ID NO: 4:

W13F, L, I, V, Y, A;
G48A, V, S, T, I, L;
*48aD or *48aY (i.e., insertion of D or Y);
T49X;
*49aX (i.e., insertion of any possible amino acid residue)
S50X, in particular D, Y, L, T, V, I;
Q51R, K;
A52X, in particular A52S, N, T, F, L, I, V;

D53E, Q, Y, I, N, S, T, V, L;
V54X, in particular V54I, N, W, Y, F, L;
G57S, A, V, L, I, F, Y, T;
G107X, in particular G107A, V, S, T, I, L, C;
G108X, in particular G108A, V, S, T, I, L;
A111V, I, L;
S168Y;
M197X, in particular Y, F, L, I, T, A, G.

In a preferred embodiment a variant of the invention comprises the following mutations corresponding to the following mutations in the amino acid sequence shown in SEQ ID HO: 4:

T49X+A52X+V54N/I/L/Y/F/W+G107A, and may further comprise G108A.

In a preferred embodiment a variant of the invention comprises at least one mutation corresponding to the following mutations in the amino acid sequence shown in SEQ ID NO: 4:

T49L+G107A;
T49I+G107A;
T49L+G107A+V54I;
T49I+G107A+V54I;
A52S+V54N+T49L+G107A;
A52S+V54I+T49L+G107A;
A52S+T49L+G107A;
A52T+T49L+G107A;
A52 S+V54N+T49I+G107A;
A52S+V54I+T49I+G107A;
A52S+T49I+G107A;
T49L+G108A;
T49I+G108A;
T49L+G108A+V54I;
T49I+G108A+V54I.

All of the above-mentioned variants of the invention have altered properties (meaning increased or decreased properties), in particular at least one of the following properties relative to the parent alpha-amylase: reduced ability to cleave a substrate close to the branching point, improved substrate specificity and/or improved specific activity, altered substrate binding, altered thermal stability, altered pH/activity profile, altered pH/stability profile, altered stability towards oxidation, altered $Ca^{2+}$ dependency.

Stability

In the context of the present invention, mutations (including amino acid substitutions and/or deletions) of importance with respect to achieving altered stability, in particular improved stability (i.e., higher or lower), at especially low pH (i.e., pH 4-6) include any of the mutations listed in the in "Altered properties" section, above and the variants mentioned right below.

The following variants: Q360A, K; N102A, N326A, L, N190G, N190K; Y262A, K, E (using the BAN, i.e., SEQ ID N: 6, numbering) were also tested for pH stability. A preferred parent alpha-amylase may be BA2 described above. The pH stability was determined as described in the "Materials & Methods" section.

$Ca^{2+}$ Stability

Altered $Ca^{2+}$ stability means the stability of the enzyme under $Ca^{2+}$ depletion has been improved, i.e., higher or lower stability. In the context of the present invention, mutations (including amino acid substitutions) of importance with respect to achieving altered $Ca^{2+}$ stability, in particular improved $Ca^{2+}$ stability, i.e., higher or lower stability, at especially low pH (i.e., pH 4-6) include any of the mutations listed in the in "Altered properties" section above.

Specific Activity

In a further aspect of the present invention, important mutations with respect to obtaining variants exhibiting altered specific activity, in particular increased or decreased specific activity, especially at temperatures from 60-100° C., preferably 70-95° C., especially 80-90° C., include any of the mutations listed in the in "Altered properties" section above.

The specific activity of LE174 and LE429 was determined to 16,000 NU/mg using the Phadebas® assay described in the "Materials and Methods" section.

Altered Cleavage Pattern

In the starch liquefaction process it is desirable to use an alpha-amylase, which is capable of degrading the starch molecules into long, branched oligosaccharides, rather than an alpha-amylase, which gives rise to formation of shorter, branched oligosaccharides (like conventional Termamyl-like alpha-amylases). Short, branched oligosaccharides (panose precursors) are not hydrolyzed satisfactorily by pallalanases, which are used after alpha-amylase treatment in the liquefaction process, or simultaneously with a saccharifying amyloglucosidase (glucoamylase), or before adding a saccharifying amyloglucosidase (glucoamylase). Thus, in the presence of panose precursors, the product mixture present after the glucoamylase treatment contains a significant proportion of short, branched, so-called limit-dextrin, viz. the trisaccharide panose. The presence of panose lowers the saccharification yield significantly and is thus undesirable.

It has been reported previously (U.S. Pat. No. 5,234,823) that, when saccharifying with glucoamylase and pullulanase, the presence of residual alpha-amylase activity arising from the liquefaction process, can lead to lower yields of glucose, if the alpha-amylase is not inactivated before the saccharification stage. This inactivation can be typically carried out by adjusting the pH to below 4.7 at 95° C., before lowering the temperature to 60° C. for saccharification.

The reason for this negative effect on glucose yield is not fully understood, but it is assumed that the liquefying alpha-amylase (for example Termamyl 120 L from *B. licheniformis*) generates "limit dextrins" (which are poor substrates for pullulanase), by hydrolysing 1,4-alpha-glucosidic linkages close to and on both sides of the branching points in amylopectin. Hydrolysis of these limit dextrins by glucoamylase leads to a build up of the trisaccharide panose, which is only slowly hydrolysed by glucoamylase.

The development of a thermostable alpha-amylase, which does not suffer from this disadvantage, would be a significant improvement, as no separate inactivation step would be required.

Thus, the aim of the present invention is to arrive at a mutant alpha-amylase having appropriately modified starch-degradation characteristics but retaining the thermostability of the parent Termamyl-like alpha-amylase.

Accordingly, the invention relates to a variant of a Termamyl-like alpha-amylase, which has an improved reduced ability to cleave a substrate close to the branching point, and further has improved substrate specificity and/or improved specific activity.

Of particular interest is a variant, which cleaves an amylopectin substrate, from the reducing end, more than one glucose unit from the branching point, preferably more than two or three glucose units from the branching point, i.e., at a further distance from the branching point than that obtained by use of a wild type *B. licheniformis* alpha-amylase.

It may be mentioned here that according to WO 96/23874, variants comprising at least one of the following mutations are expected to prevent cleavage close to the branching point:

V54L, I, F, Y, W, R, K, H, E, Q;
D53L, I, F, Y, W;
Y56W;
Q333W;
Q57, all possible amino acid residues;
A52, amino acid residues larger than A, e.g., A52W, Y, L, F, I.

Mutations of particular interest in relation to obtaining variants according to the invention having an improved reduced ability to cleave a substrate close to the branching point, and further has improved substrate specificity and/or improved specific activity include mutations at the following positions in *B. licheniformis* alpha-amylase, SEQ ID NO: 4:

H156, A181, N190, A209, Q264 and I201.

It should be emphasized that not only the Termamyl-like alpha-amylases mentioned specifically below may be used. Also other commercial Termamyl-like alpha-amylases can be used. An unexhaustive list of such alpha-amylases is the following: Alpha-amylases produced by the *B. licheniformis* strain described in EP 0252666 (ATCC 27811), and the alpha-amylases identified in WO 91/00353 and WO 94/18314. Other commercial Termamyl-like *B. licheniformis* alpha-amylases are Optitherm™ and Takatherm™ (available from Solvay), Maxamyl™ (available from Gist-brocades/Genencor), Spesym AA™ Spezyme Delta AA® (available from Genencor), and Keistase™ (available from Daiwa).

All Termamyl-like alpha-amylase may suitably be used as backbone for preparing variants of the invention.

In a preferred embodiment of the invention the parent Termamyl-like alpha-amylase is a hybrid alpha-amylase of SEQ ID NO: 4 and SEQ ID NO: 6. Specifically, the parent hybrid Termamyl-like alpha-amylase may be a hybrid alpha-amylase comprising the 445 C-terminal amino acid residues of the *B. licheniformis* alpha-amylase shown in SEQ ID NO: 4 and the 37 N-terminal amino acid residues of the mature alpha-amylase derived from *B. amyloliquefaciens* shown in SEQ ID NO: 6, which may suitably further have the following mutations; H156Y+A181T+N190F+A209V+Q264 S (using the numbering in SEQ ID NO: 4). This hybrid is referred to as LE174. The LE174 hybrid may be combined with a further mutation I201F to form a parent hybrid Termamyl-like alpha-amylase having the following mutations H156Y+A181T+N190F+A209V+Q264S+I201F (using SEQ ID NO: 4 for the numbering). This hybrid variant is shown in SEQ ID NO: 2 and is used in the examples below, and is referred to as LE429.

Also, LE174 or LE429 (SEQ ID NO: 2) or *B. licheniformis* alpha-amylase shown in SEQ ID NO: 4 comprising one or more of the following mutations may be used as backbone (using SEQ ID NO: 4 for the numbering of the mutations):
E119C;
S130C;
D124C;
R127C;
A52all possible amino acid residues;
S85all possible amino acid residues;
N96all possible amino acid residues;
V129all possible amino acid residues;
A269all possible amino acid residues;
A378all possible amino acid residues;
S148all possible amino acid residues, in particular S148N;
E211all possible amino acid residues, in particular E211Q;
N188all possible amino acid residues, in particular N188S, N188P
M197all possible amino acid residues, in particular M197T, M197A, M197G, M197I, M197L, H197Y, M197F, M197I;
W138all possible amino acid residues, in particular W138Y;
D207all possible amino acid residues, in particular D207Y;
H133all possible amino acid residues, in particular H133Y;
H205all possible amino acid residues, in particular H205H, H205C, H205R;
S187all possible and no acid residues, in particular S187D;
A210all possible amino acid residues, in particular A210S, A210T;
H405all possible amino acid residues, in particular H405D;
K176all possible amino acid residues, in particular K176R;
F279all possible amino acid residues, in particular F279Y;
Q298all possible amino acid residues, in particular Q298H;
G299all possible amino acid residues, in particular G299R;
L308all possible amino acid residues, in particular L808F;
T412all possible amino acid residues, in particular T412A;

Further, *B. licheniformis* alpha-amylase shown in SEQ ID NO: 4 comprising at least one of the following mutations may be used as backbone:
M15all possible amino acid residues;
A33all possible amino acid residues;

When using LE429 (shown in SEQ ID NO: 2) as the backbone (i.e., as the parent Termamyl-like alpha-amylase) by combining LE174 with the mutation I201F (SEQ ID NO: 4 numbering), the mutations/alterations, in particular substitutions, deletions and insertions, may according to the invention be made in one or more of the following positions to improve the reduced ability to cleave a substrate close to the branching point, and to improve substrate specificity and/or improved specific activity:

W13, G48, T49, S50, Q51, A52, D53, Y54, G57, G107, G108, A111, S168, M197 (using the SEQ ID NO: 4 numbering)

wherein (a) the alteration (s) are independently
 (i) an insertion of an amino acid downstream of the amino acid which occupies the position,
 (ii) a deletion of the amino acid which occupies the position, or
 (iii) a substitution of the amino acid which occupies the position with a different amino acid, (b) the variant has alpha-amylase activity and (c) each position corresponds to a position of the amino acid sequence of the parent Termamyl-like alpha-amylase having the amino acid sequence of SEQ ID NO: 4.

In a preferred embodiment a variant of the invention comprises at least one mutation in a position corresponding to the following mutations in the amino acid sequence shown in SEQ ID NO: 4:
V54N, A52S, A52S+V54N, T49L, T49+G107A, A52S+V54N+T49L+G107A, A52S+V54N+T49L, G107A, Q51R, Q51R+A52S, A52H; or
T49F+G107A, T49V+G107A, T49D+G107A, T49Y+G107A, T49S+G107A, T49N+G107A, T49I+G107A, T49L+A52S+G107A, T49L+A52T+G107A, T49L+A52F+G107A, T49L+A52L+G107A, T49L+A52I+G107A, T49L+A52V+G107A; or
T49V, T49I, T49D, T49N, T49S, T49Y, T49F, T49W, T49M, T49E, T49Q, T49K, T49R, A52T, A52L, A52I, A52V, A52M, A52F, A52Y, A52W, V54M, G107V, G07I, G107L, G107C.

In a preferred embodiment a variant of the invention comprises at least one mutation in a position corresponding to the following mutations in the amino acid sequence shown in SEQ ID NO: 4:
W13F, L, I, V, Y, A;
G48A, V, S, T, I, L;
*48aD or *48aY (i.e., insertion of D or Y);
T49X;

*49aX (i.e., insertion of any amino acid residue)
S50X, in particular D, Y, L, T, V, I;
Q51R, K;
A52X, in particular A52S, N, T, F, L, I, V;
D53E, Q, Y, I, N, S, T, V, L;
V54X, in particular V54I, N, W, Y, F, L;
G57S, A, V, L, I, F, Y, T;
G107X, in particular G107A, V, S, T, I, L, C;
G108X, in particular G108A, V, S, T, I, L;
A111V, I, L;
S168Y;
M197X, in particular Y, F, L, I, T, A, G.

In a preferred embodiment a variant of the invention comprises at least one mutation in a position corresponding to the following mutations in the amino acid sequence shown in SEQ ID NO: 4:

T49X+A52X+V54N/I/L/Y/F/W+G107A, and may further comprise G108A.

In a preferred embodiment a variant of the invention comprises at least one mutation in a position corresponding to the following mutations in the amino acid sequence shown in SEQ ID NO: 4:
T49L+G107A;
T49I+G107A;
T49L+G107A+V54I;
T49I+G107A+V54I;
A52S+V54N+T49L+G107A;
A52S+V54I+T49L+G107A;
A52S+T49L+G107A;
A52T+T49L+G107A;
A52S+V54N+T49I+G107A;
A52S+V54I+T49I+G107A;
A52S+T49I+G107A;
T49L+G108A;
T49I+G108A;
T49L+G108A+V54I;
T49I+G108A+V54I.

General Mutations in Variants of the Invention

It may be preferred that a variant of the invention comprises one or more modifications in addition to those outlined above. Thus, it may be advantageous that one or more proline residues present in the part of the alpha-amylase variant which is modified is/are replaced with a non-proline residue which may be any of the possible, naturally occurring non-proline residues, and which preferably is an alanine, glycine, serine, threonine, valine or leucine.

Analogously, it may be preferred that one or more cysteine residues present among the amino acid residues with which the parent alpha-amylase is modified is/are replaced with a non-cysteine residue such as serine, alanine, threonine, glycine, valine or leucine.

Furthermore, a variant of the invention may—either as the only modification or in combination with any of the above outlined modifications—be modified so that one or more Asp and/or Glu present in an amino acid fragment corresponding to the amino acid fragment 185-209 of SEQ ID NO. 4 is replaced by an Asn and/or Gln, respectively. Also of interest is the replacement, in the Termamyl-like alpha-amylase, of one or more of the Lys residues present in an amino acid fragment corresponding to the amino acid fragment 185-209 of SEQ ID NO: 4 by an Arg.

It will be understood that the present invention encompasses variants incorporating two or more of the above outlined modifications.

Furthermore, it may be advantageous to introduce point-mutations in any of the variants described herein.

Methods for Preparing Alpha-Amylase Variants

Several methods for introducing mutations into genes are known in the art. After a brief discussion of the cloning of alpha-amylase-encoding DNA sequences, methods for generating mutations at specific sites within the alpha-amylase-encoding sequence will be discussed.

Cloning a DNA Sequence Encoding an Alpha-Amylase

The DNA sequence encoding a parent alpha-amylase may be isolated from any cell or microorganism producing the alpha-amylase in question, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, homologous, labelled oligonucleotide probes may be synthesized and used to identify alpha-amylase-encoding clones from a genomic library prepared from the organism in question. Alternatively, a labelled oligonucleotide probe containing sequences homologous to a known alpha-amylase gene could be used as a probe to identify alpha-amylase-encoding clones, using hybridization and washing conditions of lower stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase, thereby allowing clones expressing the alpha-amylase to be identified.

Alternatively, the DNA sequence encoding the enzyme may be prepared synthetically by established standard methods, e.g., the phosphoroamidite method described by S. L. Beaucage and M. H. Caruthers (1981) or the method described by Matches et al. (1984). In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988).

Site-Directed Mutagenesis

Once an alpha-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the alpha-amylase-encoding sequence, is created in a vector carrying the alpha-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 disclose the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into alpha-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

Random mutagenesis is suitably performed either as localised or region-specific random mutagenesis in at least three parts of the gene translating to the amino acid sequence shown in question, or within the whole gene.

The random mutagenesis of a DNA sequence encoding a parent alpha-amylase may be conveniently performed by use of any method known in the art.

In relation to the above, a further aspect of the present invention relates to a method for generating a variant of a parent alpha-amylase, e.g., wherein the variant exhibits a reduced capability of cleaving an oligo-saccharide substrate close to the branching point, and further exhibits improved substrate specificity and/or improved specific activity relative to the parent, the method:

(a) subjecting a DNA sequence encoding the parent alpha-amylase to random mutagenesis,
(b) expressing the mutated DNA sequence obtained in step (a) in a host cell, and
(c) screening for host cells expressing an alpha-amylase variant which has an altered property (i.e., thermal stability) relative to the parent alpha-amylase.

Step (a) of the above method of the invention is preferably performed using doped primers. For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one, which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties. When the mutagenesis is performed by the use of an oligonucleotide, the oligonucleotide may be doped or spiked with the three non-parent nucleotides during the synthesis of the oligonucleotide at the positions, which are to be changed. The doping or spiking may be done so that codons for unwanted amino acids are avoided. The doped or spiked oligonucleotide can be incorporated into the DNA encoding the alpha-amylase enzyme by any published technique, using e.g., PCR, LCR or any DNA polymerase and ligase as deemed appropriate. Preferably, the doping is carried out using "constant random doping", in which the percentage of wild type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program, which, inter alia, ensures that introduction of stop codons is avoided. When PCR-generated mutagenesis is used, either a chemically treated or non-treated gene encoding a parent alpha-amylase is subjected to PCR under conditions that increase the mis-incorporation of nucleotides (Deshler 1992; Leung et al., Technique, Vol. 1, 1989, pp. 11-15). A mutator strain of E. coli (Fowler et al., Molec. Gen. Genet., 133, 1974, pp. 179-191), S. cereviseae or any other microbial organism may be used for the random mutagenesis of the DNA encoding the alpha-amylase by, e.g., transforming a plasmid containing the parent glycosylase into the mutator strain, growing the mutator strain with the plasmid and isolating the mutated plasmid from the mutator strain. The mutated plasmid may be subsequently transformed into the expression organism. The DNA sequence to be mutagenized may be conveniently present in a genomic or cDNA library prepared from an organism expressing the parent alpha-amylase. Alternatively, the DNA sequence may be present on a suitable vector such as a plasmid or a bacteriophage, which as such may be incubated with or otherwise exposed to the mutagenising agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence. In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme. Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gram-negative bacteria such as *E. coli*. The mutated DNA sequence may further comprise a DNA sequence encoding functions permitting expression of the mutated DNA sequence.

Localised Random Mutagenesis

The random mutagenesis may be advantageously localised to a part of the parent alpha-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localised, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Alternative Methods of Providing Alpha-Amylase Variants

Alternative methods for providing variants of the invention include gene-shuffling method known in the art including the methods e.g., described in WO 95/22625 (from Affymax Technologies N.V.) and WO 96/00343 (from Novo Nordisk A/S).

Expression of Alpha-Amylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an alpha-amylase variant of the invention may be any vector, which may conveniently be subjected to recombinant DNA procedures, and the choice of vector will often depend on the host cell into which it is to be introduced. Thus, the vector may be an autonomously replicating vector, i.e., a vector, which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the DNA sequence encoding an alpha-amylase variant of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* glucoamylase, *Rhizomucor miehei* lipase, A, oryzae alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g., a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* alpha-amylases mentioned herein comprise a pre-region permitting secretion of the expressed protease into the culture medium. If desirable, this pre-region may be replaced by a different preregion or signal sequence, conveniently accomplished by substitution of the DNA sequences encoding the respective preregions.

The procedures used to ligate the DNA construct of the invention encoding an alpha-amylase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

The cell of the invention, either comprising a DNA construct or an expression vector of the invention as defined above, is advantageously used as a host cell in the recombinant production of an alpha-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulants, Bacillus circulars, Bacillus lautus, Bacillus megaterium, Bacillus thuringiensis,* or *Streptomyces lividans* or *Streptomyces murinus*, or gramnegative bacteria such as *E. coli*. The transformation of the bacteria may, for instance, be effected by protoplast transformation or by using competent cells in a manner known per se.

The yeast organism may favourably be selected from a species of *Saccharomyces* or *Schizosaccharomyces*, e.g., *Saccharomyces cerevisiae*. The filamentous fungus may advantageously belong to a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

In yet a further aspect, the present invention relates to a method of producing an alpha-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the alpha-amylase variant of the invention. Suitable media are available from commercial suppliers or may be prepared according to published recipes (e.g., as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

The alpha-amylase variants of this invention possess valuable properties allowing for a variety of industrial applications. In particular, enzyme variants of the invention are applicable as a component in washing, dishwashing and hard surface cleaning detergent compositions. Numerous variants are particularly useful in the production of sweeteners and ethanol, e.g., fuel, drinking or industrial ethanol, from starch, and/or for textile desizing. Conditions for conventional starch-conversion processes, including starch liquefaction and/or saccharification processes, are described in, e.g., U.S. Pat. No. 3,912,590 and in EP patent publications Nos. 252 730 and 63 909.

Production of Sweeteners from Starch:

A "traditional" process for conversion of starch to fructose syrups normally consists of three consecutive enzymatic processes, viz. a liquefaction process followed by a saccharification process and an isomerization process. During the liquefaction process, starch is degraded to dextrins by an alpha-amylase (e.g., Termamyl™) at pH values between 5.5 and 6.2 and at temperatures of 95-160° C. for a period of approx. 2 hours. In order to ensure optimal enzyme stability under these conditions, 1 mM of calcium is added (40 ppm free calcium ions).

After the liquefaction process the dextrins are converted into dextrose by addition, of a glucoamylase (e.g., AMG™) and a debranching enzyme, such as an isoamylase or a pullulanase (e.g., Promozyme™). Before this step the pH is reduced to a value below 4.5, maintaining the nigh temperature (above 95° C.), and the liquefying alpha-amylase activity is denatured. The temperature is lowered to 60° C., and glucoamylase and debranching enzyme are added. The saccharification process proceeds for 24-72 hours.

After the saccharification process the pH is increased to a value in the range of 6-8, preferably pH 7.5, and the calcium is removed by ion exchange. The dextrose syrup is then converted into high fructose syrup using, e.g., an immunobilized glucoseisomerase (such as Sweetzyme™).

At least one enzymatic improvement of this process could be envisaged: Reduction of the calcium dependency of the liquefying alpha-amylase. Addition of free calcium is required to ensure adequately high stability of the alpha-amylase, but free calcium strongly inhibits the activity of the glucoseisomerase and needs to be removed, by means of an expensive unit operation, to an extent, which reduces the level of free calcium to below 3-5 ppm. Cost savings could be obtained if such an operation could be avoided and the liquefaction process could be performed without addition of free calcium ions.

To achieve that, a less calcium-dependent Termamyl-like alpha-amylase which is stable and highly active at low concentrations of free calcium (<40 ppm) is required. Such a Termamyl-like alpha-amylase should have a pH optimum at a pH in the range of 4.5-6.5, preferably in the range of 4.5-5.5.

The invention also relates to a composition comprising a mixture of one or more variants of the invention derived from (as the parent Termamyl-like alpha-amylase) the *B. stearothermophilus* alpha-amylase having the sequence shown in SEQ ID NO: 8 and a Termamyl-like alpha-amylase derived from the *B. licheniformis* alpha-amylase having the sequence shown in SEQ ID NO: 4.

Further, the invention also relates to a composition comprising a mixture of one or more variants according the invention derived from (as the parent Termamyl-like alpha-amylase) the *B. stearothermophilus* alpha-amylase having the sequence shown in SEQ ID NO: 8 and a hybrid alpha-amylase comprising a part of the *B. amyloliquefaciens* alpha-amylase shown in SEQ ID NO: 6 and a part of the *B. licheniformis* alpha-amylase shown in SEQ ID NO: 4. The latter mentioned hybrid Termamyl-like alpha-amylase comprises the 445 C-terminal amino acid residues of the *B. licheniformis* alpha-amylase shown in SEQ ID NO: 4 and the 37 N-terminal amino acid residues of the alpha-amylase derived from *B. amyloliquefaciens* shown in SEQ ID NO: 6. Said latter mentioned hybrid alpha-amylase may suitably comprise the following mutations: H156Y+A181T+N190F+A209V+Q264S (using the numbering in SEQ ID NO: 4) Preferably, said latter mentioned hybrid alpha-amylase may suitably comprise the following mutations: H156Y+A181T+N190F+A209V+Q264S+I201F (using the SEQ ID NO: 4 numbering), in the examples below said last-mentioned parent hybrid Termamyl-like alpha-amylase referred to as LE429 (shown in SEQ ID NO: 2) is used for preparing variants of the invention, which variants may be used in compositions of the invention.

An alpha-amylase variant of the invention or a composition of the invention may in an aspect of the invention be used for starch liquefaction, in detergent composition, such as laundry, dish wash compositions and hard surface cleaning, ethanol production, such as fuel, drinking and industrial ethanol production, desiring of textile, fabric and garments.

Materials and Methods

Enzymes:

LE174: Hybrid Alpha-Amylase Variant:

LE174 is a hybrid Termamyl-like alpha-amylase being identical to the Termamyl sequence, i.e., the *Bacillus licheniformis* alpha-amylase shown in SEQ ID NO: 4, except that the N-terminal 35 amino acid residues (of the mature protein) has been replaced by the N-terminal 33 residues of BAN (mature protein), i.e., the *Bacillus amyloliquefaciens* alpha-amylase shown in SEQ ID NO: 6, which further have following mutations:
H156Y+A181T+N190F+A209V+Q264S (SEQ ID NO: 4).
LE429 Hybrid Alpha-Amylase Variant:

LE429 is a hybrid Termamyl-like alpha-amylase being identical to the Termamyl sequence, i.e., the *Bacillus licheniformis* alpha-amylase shown in SEQ ID NO: 4, except that the N-terminal 35 amino acid residues (of the mature protein) has been replaced by the N-terminal 33 residues of BAN (mature protein), i.e., the *Bacillus amyloliquefaciens* alpha-amylase shown in SEQ ID NO: 6, which further have following mutations:
H156Y+A181T+N190F+A209V+Q264S+I201F (SEQ ID NO: 4). LE429 is shown as SEQ ID NO: 2 and was constructed by SOE-PCR (Higuchi et al. 1988, Nucleic Acids Research 16:7351).

Dextrozyme™ E: a balanced mixture of glucoamylase (AMG) and pullulanase obtainable from selected strains of *Aspergillus niger* and *Bacillus deramificans* (available from Novo Nordisk A/S)

Fermentation and Purification of Alpha-Amylase Variants

A *B. subtilis* strain harbouring the relevant expression plasmid is streaked on an LB-agar plate with 10 micro g/ml kanamycin from −80° C. stock, and grown overnight at 37° C.

The colonies are transferred to 100 ml BPX media supplemented with 10 micro g/ml kanamycin in a 500 ml shaking flask.

Composition of BPX Medium:

| | |
|---|---|
| Potato starch | 100 g/l |
| Barley flour | 50 g/l |
| BAN 5000 SKB | 0.1 g/l |
| Sodium caseinate | 10 g/l |
| Soy Bean Meal | 20 g/l |
| $Na_2HPO_4$, 12 $H_2O$ | 9 g/l |
| Pluronic ™ | 0.1 g/l |

The culture is shaken at 37° C. at 270 rpm for 5 days.

Cells and cell debris are removed from the fermentation broth by centrifugation at 4500 rpm in 20-25 minutes. Afterwards the supernatant is filtered to obtain a completely clear solution. The filtrate is concentrated and washed on an UF-filter (10000 cut off membrane) and the buffer is changed to 20 mM Acetate pH 5.5. The UF-filtrate is applied on a S-sepharose F.F. and elation is carried out by step elation with 0.2M NaCl in the same buffer. The eluate is dialysed against 10 mM Tris, pH 9.0 and applied on a Q-sepharose F.F. and eluted with a linear gradient from 0-0.3M NaCl over 6 column volumes. The fractions that contain the activity (measured by the Phadebas assay) are pooled, pH was adjusted to pH 7.5 and remaining color was removed by a treatment with 0.5% W/vol. active coal in 5 minutes.

Activity Determination—(KNU)

One Kilo alpha-amylase Unit (1 KNU) is the amount of enzyme which breaks down 5.26 g starch (Merck, Amylum Solubile, Erg. B 6, Batch 9947275) per hour in Novo Nordisk's standard method for determination of alpha-amylase based upon the following condition:

| | |
|---|---|
| Substrate | soluble starch |
| Calcium content in solvent | 0.0043M |
| Reaction time | 7-20 minutes |
| Temperature | 37° C. |
| pH | 5.6 |

Detailed description of Novo Nordisk's analytical method (AF 9) is available on request.

Assay for Alpha-Amylase Activity

Alpha-Amylase activity is determined by a method employing Phadebas® tablets as substrate. Phadebas tablets (Phadebas® Amylase Test, supplied by Pharmacia Diagnostic) contain a cross-linked insoluble blue-coloured starch polymer, which has been mixed with bovine serum albumin and a buffer substance and tableted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolysed by the alpha-amylase giving soluble blue fragments. The absorbance of the resulting blue solution, measured spectrophotometrically at 620 nm, is a function of the alpha-amylase activity.

It is important that the measured 620 nm absorbance after 10or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyse a certain amount of substrate and a blue colour will be produced. The colour intensity is measured at 620 nm. The measured absorbance is directly proportional to the specific activity (activity/mg of pure alpha-amylase protein) of the alpha-amylase in question under the given set of conditions.

Determining Specific Activity

The specific activity is determined using the Phadebas assay (Pharmacia) as activity/mg enzyme.

Measuring the pH Activity Profile (pH Stability)

The variant is stored in 20 mM TRIS ph 7.5, 0.1 mM, $CaCl_2$ and tested at 30?C, 50 mM Britton-Robinson, 0.1 mM $CaCl_2$. The pH activity is measured at pH 4.0, 4.5, 5.0, 5.5, 6.0, 7.0, 8.0, 9.5, 9.5, 10, and 10.5, using the Phadebas assay described above.

Determination of AGU Activity and As AGU/mg

One Novo Amyloglucosidase Unit (AGU) is defined as the amount of enzyme, which hydrolyzes 1 micromole maltose per minute at 37° C. and pH 4.3. A detailed description of the analytical method (AEL-SM-0131) is available on request from Novo Nordisk.

The activity is determined as AGU/ml by a method modified after (AEL-SM-0131) using the Glucose GOD-Perid kit from Boehringer Mannheim, 124036. Standard: AMG-standard, batch 7-1195, 195 AGU/ml.

375 microL substrate (1% maltose in 50 mM Sodium acetate, pH 4.3) is incubated 5 minutes at 37° C. 25 microL enzyme diluted in sodium acetate is added. The reaction is stopped after 10 minutes by adding 100 microL 0.25 M NaOH. 20 microL is transferred to a 96 well microtitre plate and 200 microL GOD-Perid solution is added. After 30 minutes at room temperature, the absorbance is measured at 650 nm and the activity calculated in AGU/ml from the AMG-standard.

The specific activity in AGU/mg is then calculated from the activity (AGU/ml) divided with the protein concentration (mg/ml).

EXAMPLES

Example 1

Construction of Termamyl Variants in Accordance with the Invention

Termamyl (*B. licheniformis* alpha-amylase SEQ ID NO: 4) is expressed in *B. subtilis* from a plasmid denoted pDN1528. This plasmid contains the complete gene encoding Termamyl, amyL, the expression of which is directed by its own promoter. Further, the plasmid contains the origin of replication, ori, from plasmid pUB110 and the cat gene from plasmid pC194 conferring resistance towards chloramphenicol. pDN1528 is shown in FIG. 9 of WO 96/23874. A specific mutagenesis vector containing a major part of the coding region of SEQ ID NO: 3 was prepared. The important features of this vector, denoted pJeEN1, include an origin of replication derived from the pUC plasmids, the cat gene conferring resistance towards chloramphenicol, and a frameshift-containing version of the bla gene, the wild type of which normally confers resistance towards ampicillin (amp$^R$ phenotype). This mutated version results in an amp$^S$ phenotype. The plasmid pJeEN1 is shown in FIG. 10 of WO 96/23874, and the *E. coli* origin of replication, ori, bla, cat, the 5'-truncated version of the Termamyl amylase gene, and selected restriction sites are indicated on the plasmid.

Mutations are introduced in amyL by the method described by Deng and Nickoloff (1992, *Anal. Biochem.* 200, pp. 81-88) except that plasmids with the "selection primer" (primer #6616; see below) incorporated are selected based on the amp$^R$ phenotype of transformed *E. coli* cells harboring a plasmid with a repaired bla gene, instead of employing the selection by restriction enzyme digestion outlined by Deng and Nickoloff. Chemicals and enzymes used for the mutagenesis were obtained from the ChameleonÔ mutagenesis kit from Stratagene (catalogue number 200509).

After verification of the DNA sequence in variant plasmids, the truncated gene, containing the desired alteration, is subcloned into pDN1528 as a PstI-EcoRI fragment and transformed into the protease- and amylase-depleted *Bacillus subtilis* strain SHA273 (described in WO92/11357 and WO95/10603) in order to express the variant enzyme.

The Termamyl variant V54W was constructed by the use of the following mutagenesis primer (written 5' to 3', left to right):

(SEQ ID NO: 9)
PG GTC GTA GGC ACC GTA GCC CCA ATC CGC TTG

The Termamyl variant A52W+V54W was constructed by the use of the following mutagenesis primer (written 5' to 3', left to right):

(SEQ ID NO: 10)
PG GTC GTA GGC ACC GTA GCC CCA ATC CCA TTG GCT CG

Priemer #6616 (written 5' to 3', left to right ; P denotes a 5' phosphate):

(SEQ ID NO: 11)
P CTG TGA CTG GTG AGT ACT CAA CCA AGT C

The Termamyl variant V54E was constructed by the use of the following mutagenesis primer (written 5'-3', left to right):

(SEQ ID NO: 12)
PGG TCG TAG GCA CCG TAG CCC TCA TCC GCT TG

The Termamyl variant V54M was constructed by the use of the following mutagenesis primer (written 5'-3', left to right):

(SEQ ID NO: 13)
PGG TCG TAG GCA CCG TAG CCC ATA TCC GCT TG

The Termamyl variant V54I was constructed by the use of the following mutagenesis primer (written 5'-3', left to right):

(SEQ ID NO: 14)
PGG TCG TAG GCA CCG TAG CCA ATA TCC GCT TG

The Termamyl variants Y290E and Y290K were constructed by the use of the following mutagenesis primer (written 5'-3', left to right):

(SEQ ID NO: 15)
PGC AGC ATG GAA CTG CTY ATG AAG AGG CAC GTC AAA C

Y represents an equal mixture of C and T. The presence of a codon encoding either Glutamate or Lysine in position 290 was verified by DNA sequencing.

The Termamyl variant N190F was constructed by the use of the following mutagenesis primer (written 5'-3', left to right):

(SEQ ID NO: 16)
PCA TAG TTG CCG AAT TCA TTG GAA ACT TCC C

The Termamyl variant N188P+N190F was constructed by the use of the following mutagenesis primer (written 5'-3', left to right):

(SEQ ID NO: 17)
PCA TAG TTG CCG AAT TCA GGG GAA ACT TCC CAA TC

The Termamyl variant H140K+H142D was constructed by the use of the following mutagenesis primer (written 5'-3', left to right):

(SEQ ID NO: 18)
PCC GCG CCC CGG GAA ATC AAA TTT TGT CCA GGC TTT AAT TAG

The Termamyl variant H156Y was constructed by the use of the following mutagenesis primer (written 5'-3', left to right):

(SEQ ID NO: 19)
PCA AAA TGG TAC CAA TAC CAC TTA AAA TCG CTG

The Termamyl variant A181T was constructed by the use of the following mutagenesis primer (written 5'-3', left to right):

```
                                    (SEQ ID NO: 20)
   PCT TCC CAA TCC CAA GTC TTC CCT TGA AAC
```

The Termamyl variant A209V was constructed by the use of the following mutagenesis primer (written 5'-3', left to right):

```
                                    (SEQ ID NO: 21)
PCTT AAT TTC TGC TAC GAC GTC AGG ATG GTC ATA ATC
```

The Termamyl variant Q264S was constructed by the use of the following mutagenesis primer (written 5'-3', left to right):

```
                                    (SEQ ID NO: 22)
PCG CC AAG TCA TTC GAC CAG TAC TCA GCT ACC GTA AAC
```

The Termamyl variant S187D was constructed by the use of the following mutagenesis primer (written 5'-3', left to right):

```
                                    (SEQ ID NO: 23)
    PGC CGT TTT CAT TGT CGA CTT CCC AAT CCC
```

The Termamyl variant DELTA (K370-G371-D372) (i.e., deleted of amino acid residues nos. 370, 371 and 372) was constructed by the use of the following mutagenesis primer (written 5'-3', left to right):

```
                                    (SEQ ID NO: 24)
PGG AAT TTC GCG CTG ACT AGT CCC GTA CAT ATC CCC
```

The Termamyl variant DELTA (D372-S373-Q374) was constructed by the use of the following mutagenesis primer (written 5'-3', left to right):

```
                                    (SEQ ID NO: 25)
PGG CAG GAA TTT CGC GAC CTT TCG TCC CGT ACA TAT C
```

The Termamyl variants A181T and A209V were combined to A181T+A209V by digesting the A131T containing pDN1528-like plasmid (i.e., pDN1528 containing within amyL the mutation resulting in the A181T alteration; and the A209V-containing pDN1528-like plasmid (i.e., pDN1528 containing within amyL the mutation resulting in the A209V alteration) with restriction enzyme ClaI which cuts the pDN1528-like plasmids twice resulting in a fragment of 1116 bp and the vector-part (i.e. contains the plasmid origin of replication) of 3850 bp. The fragment containing the A209V mutation and the vector part containing the A181T mutation were purified by QIAquick gel extraction kit (purchased from QIAGEN) after separation on an agarose gel. The fragment and the vector were ligated and transformed into the protease and amylase depleted *Bacillus subtilis* strain referred to above. Plasmid from amy+ (clearing zones on starch containing agar-plates) and chloramphenicol resistant transformants were analysed for the presence of both mutations on the plasmid.

In a similar way as described above, H156Y and A209V were combined utilizing restriction endonucleases Acc65I and EcoRI, giving H156Y+A209V.

H156Y+A209V and A181T+A209V were combined into H156Y+A181T+A209V by the use of restriction endonucleases Acc65I and HindIII.

The 35 N-terminal residues of the mature part of Termamyl variant H156Y+A181T+A209V were substituted by the 33 N-terminal residues of the *B. amyloliquefaciens* alpha-amylase (SEQ ID NO: 4) (which in the present context is termed BAN) by a SOE-PCR approach (Higuchi et al. 1938, Nucleic Acids Research 16:7351) as follows:

```
Primer 19364 (sequence 5'-3'):
                                    (SEQ ID NO: 26)
CCT CAT TCT GCA GCA GCA GCC GTA AAT GGC ACG CTG Primer 19362:
                                    (SEQ ID NO: 27)
CCA GAC GGC AGT AAT ACC GAT ATC CGA TAA ATG TTC CG Primer 19363:
                                    (SEQ ID NO: 28)
CGG ATA TCG GTA TTA CTG CCG TCT GGA TTC Primer 1C:
                                    (SEQ ID NO: 29)
CTC GTC CCA ATC GGT TCC GTC
```

A standard PCR, polymerase chain reaction, was carried out using the Pwo thermostable polymerase from Boehringer Mannheim according to the manufacturer's instructions and the temperature cyclus: 5 minutes at 94° C., 25 cycles of (94° C. for 30 seconds, 50° C. for 45 seconds, 72° C. for 1 minute), 72° C. for 10 minutes.

An approximately 130 bp fragment was amplified in a first PCR denoted PCR1 with primers 19364 and 19362 on a DNA fragment containing the gene encoding the *B. amyloliquefaciens* alpha-amylase.

An approximately 400 bp fragment was amplified in another PCR denoted PCR2 with primers 19363 and 1C on template pDN1528.

PCR1 and PCR2 were purified from an agarose gel and used as templates in PCR3 with primers 19364 and 1C, which resulted in a fragment of approximately 520 bp. This fragment thus contains one part of DNA encoding the N-terminus from BAH fused to a part of DNA encoding Termamyl from the 35th amino acid.

The 520 bp fragment was subcloned into a pDN1528-like plasmid (containing the gene encoding Termamyl variant H156Y+A181T+A209V) by digestion with restriction endonucleases PstI and SacII, ligation and transformation of the *B. subtilis* strain as previously described. The DNA sequence between restriction sites PstI and SacII was verified by DNA sequencing in extracted plasmids from amy+ and chloramphenicol resistant transformants.

The final construct containing the correct N-terminus from BAN and H156Y+A131T+A209V was denoted BAN(1-35)+H156Y+A181T+A209V.

N190F was combined with BAN(1-35)+H156Y+A181T+A209V giving BAN(1-35)+H156Y+A181T+N190F+A209V by carrying out mutagenesis as described above except that the sequence of amyL in pJeEN1 was substituted by the DNA sequence encoding Termamyl variant BAN(1-35)+H156Y+A181T+A209V Q264S was combined with BAN(1-35)+H156Y+A181T+A209V giving BAN(1-35)+H156Y+A181T+A209V+Q264S by carrying out mutagenesis as described above except that the sequence of amyL in pJeEN was substituted by the DNA sequence encoding Termamyl variant BAN(1-35)+H156Y+A181T+A209V BAN(1-35)+H156Y+A181T+A209V+Q264S and BAN(1-35)+H156Y+A181T+N190F+A209V were combined into BAN(1-35)+H156Y+A181T+N190F+A209V+Q264S utilizing restriction endonucleases BsaHI (BsaHI site was introduced close to the A209V mutation) and PstI. I201F was combined with BAN(1-35)+H156Y+A181T+N190F+A209V+Q264S giving BAN(1-35)+H156Y+A181T+N190F+A209V+Q264S+I201F (SEQ ID NO: 2) by carrying out mutagenesis as described above. The mutagenesis primer AM100 was used, introduced the I201F substitution and removed simultaneously a Cla I restriction site, which facilitates easy pin-pointing of mutants.

```
primer AM100:
5' GATGTATGCCGACTTCGATTATGACC 3'   (SEQ ID NO: 30
```

Example 2

Construction of Termamyl-Like Alpha-Amylase Variants with an Altered Cleavage Pattern According to the Invention The variant of the thermostable *B. licheniformis* alpha-amylase consisting comprising the 445 C-terminal amino acid residues of the *B. licheniformis* alpha-amylase shown in SEQ ID NO: 4 and the 37 N-terminal amino acid residues of the alpha-amylase derived from *B. amyloliquefaciens* shown in SEQ ID NO: 6, and further comprising the following mutations:

H156Y+A181T+N190F+A209V+Q264S+I201F (the construction of this variant is described in Example 1, and the amino acid sequence shown in SEQ ID NO: 2) has a reduced capability of cleaving an substrate close to the branching point.

In an attempt to further improve the reduced capability of cleaving an substrate close to the branching point of said alpha-amylase variant site directed mutagenesis was carried out using the Mega-primer method as described by Sarkar and Sommer, 1990 (BioTechniques 8: 404-407):

Construction of LE313: BAN/Termamyl Hybrid+H156Y+A181T+N190 F+A209V+Q264S+V54N:

Gene specific primer 27274 and mutagenic primer AM115 are used to amplify by PCR an approximately 440 bp DNA fragment from a pDN1528-like plasmid (harbouring the BAN (1-35)+H156Y+A181T+N190F+I201F+A209V+Q264S mutations in the gene encoding the amylase from SEQ ID NO: 4).

The 440 bp fragment is purified from an agarose gel and used as a Mega-primer together with primer 113711 in a second PCR carried out on the same template.

The resulting approximately 630 bp fragment is digested with restriction enzymes EcoR V and Acc65 I and the resulting approximately 370 bp DNA fragment is purified and ligated with the pDN1528-like plasmid digested with the same enzymes. Competent *Bacillus subtilis* SHA273 (amylase and protease low) cells are transformed with the ligation and Chloramphenicol resistant transformants are checked by DNA sequencing to verify the presence of the correct mutations on the plasmid.

```
Primer 27274:
                                   (SEQ ID NO: 31)
5' CATAGTTGCCGAATTCATTGGAAACTTCCC 3'

Primer 1B:
                                   (SEQ ID NO: 32)
5' CCGATTGCTGACGCTGTTATTTGC 3'
```

```
                           -continued
primer AM115:
                                   (SEQ ID NO: 33)
5' GCCAAGCGGATAACGGCTACGGTGC 3'
```

Construction of LE314: BAN/Termamyl hybrid+H156Y+A181T+N190F+A209V+Q264S+A52S is carried our in a similar way, except that mutagenic primer AM116 is used.

```
AM116:
5' GAACGAGCCAATCGGACGTGGGCTACGG 3' (SEQ ID NO: 34)
```

Construction of LE315: BAN/Termamyl hybrid+H156Y+A181T+N190F+A209V+Q264S+A52S+V54N is carried our in a similar way, except that mutagenic primer AM117 is used.

```
AM117:
                                   (SEQ ID NO: 35)
5' GGAACGAGCCAATCGGATAACGGCTACGGTGC 3'
```

Construction of LE316: BAN/Termamyl hybrid+H156Y+A181T+N190F+A209V+Q264S+T49L is carried our in a similar way, except that mutagenic primer AM118 is used.

```
AM118:
5' GCATATAAGGGACTGAGCCAAGCGG 3'   (SEQ ID NO: 36)
```

Construction LE317: BAN/Termamyl hybrid+H156Y+A181T+N190F+A209V+Q264S+T49L+G107A is carried our in a similar way, except that mutagenic primer AM118 and mutagenic primer AM119 are used simultaneously.

```
AM119:
5' CAACCACAAAGCCGGCGCTGATGCG 3'   (SEQ ID NO: 37)
```

Construction of LE318: BAN/Termamyl hybrid+H156Y+A181T+N190F+A209V+Q264S+A52S+V54N+T49L+G107A is carried our in a similar way, except that mutagenic primer AM120 and mutagenic primer AM119 are used simultaneously.

```
AM120:
                                   (SEQ ID NO: 38)
5' GCATATAAGGGACTGAGCCAATCGGATAACGGCTACGGTGC 3'
```

Construction of LE 319: BAN/Termamyl hybrid+H156Y+A181T+H190F+A209V+Q264S+A52S+V54N+T49L is carried our in a similar way, except that mutagenic primer AM120 is used.

Construction of LE320: BAN/Termamyl hybrid+H156Y+A181T+N190F+A209V+Q264S+G107A is carried our in a similar way, except that mutagenic primer AM119 is used.

Construction of LE322: BAN/Termamyl hybrid+H156Y+A181T+N190F+A209V+Q264S+Q51R+A52S is carried our in a similar way, except that mutagenic primer AM121 is used.

```
AM121:
5' GAACGAGCCGATCGGACGTGGGCTACGG 3' (SEQ ID NO: 39)
```

Construction of LE323: BAN/Termamyl hybrid+H156Y+A181T+N190F+A209V+Q264S+A52N is carried our in a similar way, except that mutagenic primer AM122 is used.

AM122:
5' GAACGAGCCAAAACGACGTGGGCTACGG 3' (SEQ ID NO: 40)

Example 3

Testing of LE429 Variants

Saccharification

The standard reaction conditions were:

| | |
|---|---|
| Substrate concentration | 30% w/w |
| Temperature | 60° C. |
| Initial pH (at 60° C.) | 5.5 |
| Enzyme dosage | |
| Glucoamylase | 0.18 AGU/g DS |
| Pullulanase | 0.06 PUN/g DS |
| Alpha-amylase | 10 micro g enzyme/g DS |

Dextrozyme™ E was Used to Provide Glucoamylase and Pullulanase Activities

Substrates for saccharification were prepared by dissolving common corn starch in deionized water and adjusting the dry substance to approximately 30% w/w. The pH was adjusted to 5.5 (measured at 60° C.), and aliquots of substrate corresponding to 10 g dry weight were transferred to blue cap glass flasks.

The flasks were then placed in a shaking water bath equilibrated at 60° C., and the enzymes added. The pH was readjusted to 5.5 where necessary. The samples were taken after 48 hours of saccharification; the pH was adjusted to about 3.0, and then heated in a boiling water bath for 15 minutes to inactivate the enzymes. After cooling, the samples were treated with approximately 0.1 g mixed bed ion exchange resin (BIO-BAD 501 X8 (D)) for 30 minutes on a rotary mixer to remove salts and soluble N. After filtration, the carbohydrate composition was determined toy HPLC. The following results were obtained:

The parent alpha-amylase for the variants is LE429.

| Added Alpha-amylase Variants | $DP_1$ | $DP_2$ | $DP_3$ | SPEC. ACT. (NU/mg) |
|---|---|---|---|---|
| V54N | 96.1 | 1.75 | 1.18 | 8200 |
| A52S | 95.9 | 1.80 | 1.11 | 18800 |
| A52S + V54N | 96.3 | 1.84 | 1.08 | 10000 |
| T49L | 96.3 | 1.77 | 1.11 | 12300 |
| T49L + G107A | 96.4 | 1.87 | 0.72 | 13600 |
| A52S + V54N + T49L + G107A | 80.5 | 2.55 | 0.43 | 10000 |
| A52S + V54N + T49L | 95.8 | 1.76 | 0.84 | 8400 |
| G107A | 94.4 | 1.89 | 1.04 | 19600 |
| Q51R + A523 | 95.9 | 1.77 | 1.27 | 16500 |
| A52N | 95.5 | 1.89 | 1.56 | 17600 |
| LE174 (CONTROL) | 95.9/ 95.8 | 1.87/ 1.83 | 1.17/ 1.35 | 16000 |

Compared with the control, the presence of an active alpha-amylase variant of the invention during liquefaction results in decreased panose levels (DP3).

Especially the T49L+G107A variant of LE429 and the A52S+V54N+T49L variant of LE429, respectively, result in a drastically decreased panose level ($DP_3$). If these alpha-amylase variants are used for starch liquefaction, it will not be necessary to inactivate the enzyme before the commencement of saccharification.

Example 4

Liquefaction and Saccharification of LE429 Variants

The experiment in Example 3 was repeated for a number of other LE429 variants under the same conditions.

The result is shown below:

| Variant /sugar profile | DP1 | DP2 | DP3 | DP4+ |
|---|---|---|---|---|
| T49V + G107A | 95.9% | 1.72% | 1.27% | 1.11% |
| T49Y + G107A | 95.3% | 1.73% | 1.29% | 1.65% |
| T49N + G107A | 95.7% | 1.64% | 1.51% | 1.18% |
| T49L + A52S + G107A | 95.7% | 1.73% | 0.95% | 1.67% |
| T49L + A52T + G107A | 95.8% | 1.66% | 1.03% | 1.48% |
| T49L + A52F + G107A | 95.7% | 1.69% | 1.16% | 1.42% |
| T49L + A52L + G107A | 95.5% | 1.70% | 1.40% | 1.38% |
| T49L + A52I + G107A | 95.9% | 1.72% | 1.31% | 1.07% |
| T49L + A52V + G107A | 94.7% | 1.69% | 1.16% | 2.44% |
| T49L + A52V + G107A + A111V | 94.5% | 1.75% | 0.72% | 2.99% |
| LE429 | 94.9% | 1.71% | 1.85% | 1.51% |

Example 5

The experiment in Example 3 was repeated for a number of LE429 variants, except that the liquefaction was carried out at 95?C, pH 6.0 and the saccharification at 60?C, pH 4.5, 40 ppm $CaCl_2$, followed by inactivation. The variant referred to below are LE429 variant. The results found are as follows:

| Variant/sugar profile | DP4+ | DP3 | DP2 | DP1 |
|---|---|---|---|---|
| T49F | 1.15 | 0.92 | 1.83 | 96.12 |
| T49D + G107A | 0.84 | 1.03 | 1.82 | 96.3 |
| T49I + G107A | 0.97 | 0.64 | 1.84 | 96.55 |
| T49L + G107A | 0.96 | 0.81 | 1.82 | 96.42 |
| T49L + A52S + G107A | 1.37 | 0.75 | 1.88 | 96.01 |
| T49L + A52T + G107A | 0.87 | 0.81 | 1.8 | 96.52 |
| T49L + A52F + G107A | 0.98 | 0.83 | 1.87 | 96.31 |
| T49V + G107A | 0.65 | 0.8 | 2.13 | 96.43 |
| T49Y + G107A | 0.83 | 0.94 | 1.89 | 96.35 |
| LE429 | 1.16 | 1.21 | 1.77 | 95.87 |

REFERENCES CITED

Klein, C., et al., *Biochemistry* 1992, 31, 8740-8746,

Mizuno, H., et al., *J. Mol. Biol.* (1993) 234, 1282-1283,

Chang, C., et al, *J. Mol. Biol.* (1993) 229, 235-238,

Larson, S. B., *J. Mol. Biol.* (1994) 235, 1560-1584,

Lawson, C. L., *J. Mol. Biol.* (1994) 236, 590-600,

Qian, H., et al., *J. Mol. Biol.* (1993) 231, 785-799,

Brady, R. L., et al., *Acta Crystallogr. sect. B,* 47, 527-535,

Swift, H. J., et al., *Acta Crystallogr. sect. B,* 47, 535-544

A. Kadziola, Ph.D. Thesis: "An alpha-amylase from Barley and its Complex with a Substrate Analogue Inhibitor Studied by X-ray Crystallography", Department of Chemistry University of Copenhagen 1993

MacGregor, E. A., Food Hydrocolloids, 1987, Vol. 1, No. 5-6, p.

B. Diderichsen and L. Christiansen, Cloning of a maltogenic amylase from *Bacillus stearothermophilus*, FEMS Microbiol. letters: 56; pp. 53-60 (1988)
Hudson et al., Practical Immunology, Third edition (1989), Blackwell Scientific Publications,
Sambrook et al., *Molecular Cloning: A Laboratory Manual*, 2nd Ed., Cold Spring Harbor, 1989
S. L. Beaucage and M. H. Caruthers, *Tetrahedron Letters* 22, 1981, pp. 1859-1869
Matthes et al., *The EMBO J.* 3, 1984, pp. 801-805.
R. K. Saiki et al., *Science* 239, 1988, pp. 487-491.
Morinaga et al., (1984, Biotechnology 2:646-639)
Nelson and Long, *Analytical Biochemistry* 180, 1989, pp. 147-151
Hunkapiller et al., 1984, Nature 310:105-111
R. Higuchi, B. Krummel, and R. K. Saiki (1988). A general method of in vitro preparation and specific mutagenesis of DNA fragments: study of protein and DNA interactions. *Nucl. Acids Res.* 16:7351-7367.
Dubnau et al., 1971, *J. Mol. Biol.* 56, pp. 209-221.
Gryczan et al., 1978, *J. Bacteriol.* 134, pp. 318-329.
S. D. Erlich, 1977, *Proc. Natl. Acad. Sci.* 74, pp. 1680-1682.
Boel et al., 1990, *Biochemistry* 29, pp. 6244-6249.
Sarkar and Sommer, 1990, *BioTechniques* 8, pp. 404-407.

---

The invention claimed is:

1. An isolated variant of a parent alpha-amylase, comprising a substitution at a position corresponding to position 52, wherein:

(a) the variant has alpha-amylase activity;

(b) the variant has at least 90% sequence identity with an amino acid sequence selected from the group consisting of SEQ ID NO: 2, SEQ ID NO: 4, SEQ ID NO: 6, and SEQ ID NO: 8; and (c) the amino acid sequence of SEQ ID NO: 4 is used for position numbering.

2. The variant of claim 1, wherein the substitution at a position corresponding to position 52 is A52S,N,T,F,L,I,V.

3. The variant of claim 1, wherein the substitution at a position corresponding to position 52 is A52N.

4. The variant of claim 1, further comprising a substitution at a position corresponding to position 48.

5. The variant of claim 1, further comprising a substitution at a position corresponding to position 49.

6. The variant of claim 1, further comprising a substitution at a position corresponding to position 107.

7. The variant of claim 5, further comprising a substitution at a position corresponding to position 107.

8. The variant of claim 1, further comprising G108A.

9. The variant of claim 1, further comprising one or more mutations selected from the group consisting of:
T49D,
T9D+G107A,
T9E,
T49F,
T49F+G107A,
T49I,
T49I+G107A,
T49K,
T49L,
T49L+G107A,
T49M,
T49N,
T49N+G107A,
T49Q,
T49R,
T49S,
T49S+G107A,
T49V,
T49V+G107A,
T49W,
T49Y,
T49Y+G107A,
Q51R,
V54M,
V54N,
V54N+T49L,
V54N+T49L+G107A,
G107A,
G107C,
G107I,
G107L, and
G107V.

10. The variant of claim 1, further comprising a mutation selected from the group consisting of:
W13F,L,I,V,Y,A;
G48A,V,S,T,I,L;
*48aD or *48aY;
T49X;
*49aX;
S50 D,Y,L,T,V,I;
Q51R,K;
D53E,Q,Y,I,N,S,T,V,L;
V54I,N,W,Y,F,L;
G57S,A,V,L,I,F,Y,T;
G107A,V,S,T,I,L,C;
G108A,V,S,T,I,L;
A111V,I,L;
S168Y; and
M197 Y,F,L,I,T,A,G.

11. The variant of claim 1, further comprising a mutation selected from the group consisting of:
T49I+V54I+G107A;
T49I+V54N+G107A;
T49I+G107A;
T49I+G107A;
T49I+G108A;
T49I+G108A+V54I;
T49L+V54I+G107A;
T49L+V54N+G107A;
T49L+G107A;
T49L+G108A; and
T49L+G108A+V54I.

12. The variant of claim 1, which has at least 90% sequence identity with SEQ ID NO: 2.

13. The variant of claim 1, which has at least 95% sequence identity with SEQ ID NO: 2.

14. The variant of claim 1, which has at least 90% sequence identity with SEQ ID NO: 4.

15. The variant of claim 1, which has at least 95% sequence identity with SEQ ID NO: 4.

16. The variant of claim 1, which has at least 90% sequence identity with SEQ ID NO: 6.

17. The variant of claim 1, which has at least 95% sequence identity with SEQ ID NO: 6.

18. The variant of claim 1, which has at least 90% sequence identity with SEQ ID NO: 8.

19. The variant of claim 1, which has at least 95% sequence identity with SEQ ID NO: 8.

20. The variant of claim 1, which has a reduced capability of cleaving an oligosaccharide substrate close to the branching point as compared to the parent alpha-amylase.

21. The variant of claim 1, which exhibits improved substrate specificity and/or improved specific activity relative to the parent alpha-amylase.

22. A detergent composition, comprising an alpha-amylase of claim 1 and a surfactant.

* * * * *

UNITED STATES PATENT AND TRADEMARK OFFICE
CERTIFICATE OF CORRECTION

| | | |
|---|---|---|
| PATENT NO. | : 7,867,746 B2 | Page 1 of 1 |
| APPLICATION NO. | : 11/934136 | |
| DATED | : January 11, 2011 | |
| INVENTOR(S) | : Andersen et al. | |

It is certified that error appears in the above-identified patent and that said Letters Patent is hereby corrected as shown below:

In claim 9, at column 63, line 18 please delete "T9E" and insert --T49E--.

Signed and Sealed this
Fifteenth Day of March, 2011

David J. Kappos
*Director of the United States Patent and Trademark Office*